United States Patent [19] … [11] Patent Number: 6,033,909
Uhlmann et al. … [45] Date of Patent: Mar. 7, 2000

[54] OLIGONUCLEOTIDE ANALOGS, THEIR PREPARATION AND USE

[75] Inventors: Eugen Uhlmann, Glashütten; Anuschirwan Peyman, Kelkheim, both of Germany; Gerard O'Malley, Newtown, Pa.; Matthias Helsberg, Kelkheim; Irvin Winkler, Liederbach, both of Germany

[73] Assignee: Hoechst Aktiengesellschaft, Frankfurt am Main, Germany

[21] Appl. No.: 08/281,203

[22] Filed: Jul. 27, 1994

Related U.S. Application Data

[63] Continuation-in-part of application No. 08/003,972, Jan. 19, 1993, abandoned.

[30] Foreign Application Priority Data

Jan. 22, 1992 [DE] Germany ............................ 42 01 662

[51] Int. Cl.$^7$ ................ C12Q 1/68; C07H 2/04
[52] U.S. Cl. ............... 435/375; 435/6; 435/91.1; 435/442; 536/23.1; 536/24.3; 536/24.33; 536/24.5; 536/25.3; 536/25.31
[58] Field of Search ................ 536/23.1, 25.3, 536/25.31, 25.32, 25.33, 25.34, 24.5, 24.3, 24.31, 24.32; 514/44; 436/6, 172.3

[56] References Cited

U.S. PATENT DOCUMENTS

| 4,689,320 | 8/1987 | Kaji . | |
|---|---|---|---|
| 5,214,136 | 5/1993 | Lin et al. | 514/44 |
| 5,245,022 | 9/1993 | Weis et al. | 536/27 |

FOREIGN PATENT DOCUMENTS

| 0 289 619 | 11/1988 | European Pat. Off. . | |
|---|---|---|---|
| 0 294 196 | 12/1988 | European Pat. Off. . | |
| WO 84/01778 | 5/1984 | WIPO . | |
| WO 86/07361 | 12/1986 | WIPO . | |
| 9010448 | 9/1990 | WIPO | A61K 31/70 |
| WO 91/06556 | 5/1991 | WIPO . | |
| WO 92/02638 | 2/1992 | WIPO . | |
| WO 92/06103 | 4/1992 | WIPO . | |

OTHER PUBLICATIONS

Hélène et al., Specific regulation of gene expression by antisense, sense and antigene nucleic acids, Biochimica et Biophysica Acta, vol. 1049: 99–125 (1990).

M. Ratajczak, et al., "In Vivo Treatment of Human Leukemia in a Scid Mouse Model with c–myb Antisense Oligodeoxynucleotides", Dec. 1992, Proc. Natl. Acad. Sci. USA, vol. 89, pp. 11823–11827.

G. Gray, et al., "Antisense DNA Inhibition of Tumor Growth Induced by c–Ha–ras Oncogene in Nude Mice", Feb. 1993, Cancer Research, pp. 577–580.

Osen–Sand, et al., "Inhibition of Axonal Growth by Snap–25 Antisense Oligonucleotides in vitro and in vivo", Nature, Jul. 1993, vol. 364, pp. 445–448.

Higgins, et al., "Antisense Inhibition of the p65 Subunit of NF–kB Blocks Tumorigenicity and Causes Tumor Regression", Proc. Natl. Acad. Sci. USA, Nov. 1993, vol. 90, pp. 9901–9905.

Dean, et al., "Inhibition of Protein Kinase C–α Expression in Human A549 Cells by Antisense Oligonucleotides Inhibits Induction of Intercellular Adhesion Molecule 1 (ICAM–1) mRNA by Phorbol Esters", Journ. of Biologic Chemistry, Jun. 1994, vol. 269, No. 23, pp. 16416–16424.

Shi, et al., "Transcatheter Delivery of c–myc Antisense Oligomers Reduce Neointimal Formation in a Porcine Model of Coronary Artery Balloon Injury", Aug. 1994, Circulation, vol. 90, No. 2, pp. 944–951.

Dean, et al., "Inhibition of Protein Kinase C–α Expression in Mice After Systemic Administration of Phosphorothioate Antisense Oligodeoxynucleotides", Nov. 1994, Proc. Natl. Acad. Sci. USA, vol. 91, pp. 11762–11766.

(List continued on next page.)

*Primary Examiner*—John L. LeGuyader
*Attorney, Agent, or Firm*—Finnegan, Henderson, Farabow, Garrett & Dunner, L.L.P.

[57] ABSTRACT

The invention relates to compounds of the formula I (I)

where $R^1$ is H, alkyl, acyl, aryl, or a phosphate residue; $R^2$ is H, OH, alkoxy, $NH_2$, or halogen; B is a base customary in nucleotide chemistry; a is O or $CH_2$; n is an integer from 1 to 100; W=O, S or Se; V=O, S, or NH; Y=O, S, NH, or $CH_2$; Y'=O, S, NH, or alkylene; X=OH or SH; U=OH, SH, SeH, alkyl, alkoxy, aryl, aryloxy, or amine, and Z=OH, SH, SeH, an optionally substituted radical from the group comprising alkyl, aryl, heteroaryl, alkoxy, or amino, or a group which favors intracellular uptake or serves as the label of a DNA probe or attacks the target nucleic acid during hybridization, where if Z=OH, SH, $CH_3$, or $OC_2H_5$, at least one of the groups X, Y, Y', V, or W is not OH or O or $R^1$ is not H; a process for their preparation and their use as inhibitors of gene expression, as probes for detecting nucleic acids and as aids in molecular biology.

12 Claims, 1 Drawing Sheet

OTHER PUBLICATIONS

Gillardon, et al., "Expression of c–Fos and c–Jun in the Cornea, Lens, and Retina After Ultraviolet Irradiation of the Rat Eye and Effects of Topical Antisense Oligodeoxynucleotides", British Journ. of Ophthalmology, 1995, vol. 79, pp. 277–281.

Gillardon, et al., "Inhibition of c–Fos Expression in the UV–irradiated Epidermis by Topical Application of Antisense Oligodeoxynucleotides Suppresses Activation of Proliferating Cell Nuclear Antigen", Carcinogenesis, 1995, vol. 16, No. 8, pp. 1853–1856.

Field, et al., "Antisense Oligonucleotides: Rational Drug Design for Genetic Pharmacology", Exp. Opin. Invest. Drugs, 1995, vol. 4, No. 9, pp. 799–821.

Wickstrom, "Strategies for Administering Targeted Therapeutic Oligodeoxynucleotides", Aug. 1992, Tibtech, vol. 10, pp. 281–287.

Wahlestedt, et al., "Modulation of Anxiety and Neuropeptide Y–Y1 Receptors by Antisense Oligodeoxynucleotides", 1993, vol. 259, pp. 528–531.

Offensperger, et al., "In vivo Inhibition of Duck Hepatitis B Virus Replication and Gene Expression by Phosphorothioate Modified Antisense Oligodeoxynucleotides", 1993, The EMBO J., vol. 12, No. 3, pp. 1257–1262.

Miller, P.S. and Ts'o, P.O.P., "A new approach to chemotherapy based on molecular biology and nucleic acid chemistry: Matagen (masking tape for gene expression)", Anti–Cancer Drug Design 2: 117–128 (1987).

Offensperger, W–B, et al., "In Vivo Inhibition of Duck Hepatitis B Virus Replication and Gene Expression by Phosphorothioate Modified Antisense Oligodeoxynucleotides", The EMBO Journal, vol. 12, (3): 1257–1262 (1993).

Goodchild, J., "Conjugates of Oligonucleotides and Modified Oligonucleotides: A Review of Their Synthesis and Properties," Bioconjugate Chemistry, vol. 1, No. 3: 165–187 (1990).

Uhlmann, E., et al., "Antisense Oligonucleotides: A New Therepeutic Principle", vol. 90, No. 4: 543–584 (1990).

Verspieren P., et al., "An Acridine–linked Oligodeoxynucleotide Targeted to the Common 5'end of Trypanosome mRNAs Kills Cultured Parasites," Gene, vol. 61:307–315 (1987).

Thuong, N.T., et al., "Nouvelle Methode de Preparation D'esters Phosphoriques, Renfermant un Groupe β–mercaptoethyle, Utilisables en Synthese Nucelotidique," Bulletin de la Société Chimique de France, No. 1–2:II–51–II–56 (1981).

Branch, TIBS 23:45–50, Feb. 1998.

E. Uhlmann et al., Chem. Rev., vol. 90(4) ('90) 543–584.

J. Milligan et al., J. Med. Chem., vol. 36(14) (Jul. 9, 1993) 1923–37.

C. Stein et al., Science, vol. 261 (Aug. 20, 1993) 1004–12.

B. Tseng et al., Cancer Gene Therapy, vol. 1(1) (Mar. 1994) 65–71.

P. Weszermann et al., Biomed. Biochim. Acta ('89) vol. 48(1) 85–93.

R. Weiss, Science News, vol. 139 (Feb. 16, 1991) 108–109.

D. Tidd, Br. J. Cancer, vol. 60 ('89) 343–50.

N. Thuong et al., in *Oligontides, A S Inhib. of Gene Exp.*, Ed. by J. Cohen, CRC Press, Inc., Florida, ('89) pp. 25–52.

R. Belagaje et al., Nucl. Acids Res., vol. 10(20) ('82) 6295–6302.

E. Felder et al., Tetrahedron Letris, vol. 25(36) ('84) 3967–70.

U. Asseline et al., PNAS, vol. 81 (Jun. 1984) 3297–3301.

A. Kabanor et al., FEBS Letts, vol. 259 (2) (Jan. 1990) 327–30.

D. Knorre et al. Oligonucleotides, Antisense Inhibitors . . . , Ed. by J. Cohen, (1989) CRC Press Inc., Boca Raton FL, pp. 173–196.

M. Chattenjer et al., JACS 112 ('90) 6397–9.

T. Le Doan et al. Nucl. Acids Res ('87) 15(19):7749–60.

P. Kumar et al., Tetrahedron Let.s 32(7) (91) 967–70.

D. Praseuth et al. PNAS 85 (Mar. 1988) 1349–53.

R. Morishita et al. Oligotechniques 2(1) ('94) 1–5.

W. Markiewicz et al. Phos. Sulf. & Sili. ('90) 51/52 :374.

T. Le Doan et al. Antisense Res. & Dev. ('91) 1:43–54.

R. Eritja et al. Tetrhed. Let.s 32(11) ('91) 1511–4.

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGGGCGGGGC TCCATGGGGG                                          20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CCGGAAAACA TCGCGGTTGT                                          20

(2) INFORMATION FOR SEQ ID NO:3:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:3:

GGTGCTGGTG CTGGACGACA                                                    20

(2) INFORMATION FOR SEQ ID NO:4:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

GGCCCTGCTG TTCCGTGGCG                                                    20

(2) INFORMATION FOR SEQ ID NO:5:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:5:

CGTCCATGTC GGCAAACAGC T                                                  21

(2) INFORMATION FOR SEQ ID NO:6:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:6:

GACGTTCCTC CTGCGGGAAG                                                    20

(2) INFORMATION FOR SEQ ID NO:7:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:7:

CCAGGGTACA GGTGGCCGGC                                                    20

(2) INFORMATION FOR SEQ ID NO:8:

(i) SEQUENCE CHARACTERISTICS:
           (A) LENGTH: 20 base pairs
           (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:8:

GACTAATCGG GAATGTTAAG                                                    20

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

ACACCCAATT CTGAAAATGG                                                    20

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

AGGTCCCTGT TCGGGCGCCA                                                    20

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GGGACTCCGG CGCAGCGC                                                      18

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GGCAAACTTT CTTTTCCTCC                                                    20

(2) INFORMATION FOR SEQ ID NO:13:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GGGAAGGAGG AGGATGAGG                                                        19

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGCAGTCATC CAGCTTCGGA G                                                     21

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCCGAGAACA TCATGGTCGA AG                                                    22

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGGGAAAGCC CGGCAAGGGG                                                       20

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ACTGCTGCCT CTTGTCTCAG G                                                     21

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CAATCAATGA CTTCAAGAGT TC                                                    22

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

CTCCCCCACC ACTTCCCCTC                                          20

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCTGGGAGCC ATAGCGAGG                                           19

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GCTGAAGGGC TTCTTCCTTA TTG                                     23

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: one-of(1, 2, 18)
        (D) OTHER INFORMATION: /note= "N is G modified by thioxo."

(ix) FEATURE:
        (A) NAME/KEY: misc_feature
        (B) LOCATION: 3
        (D) OTHER INFORMATION: /note= "N is C modified by thioxo."

(ix) FEATURE:
        (A) NAME/KEY: misc_feature
        (B) LOCATION: 19
        (D) OTHER INFORMATION: /note= "N is T modified by thioxo."

(ix) FEATURE:
        (A) NAME/KEY: modified_base
        (B) LOCATION: 20
        (D) OTHER INFORMATION: /note= "N is C modified by OH."

(xi) SEQUENCE DESCRIPTION: SEQ ID NO:22:

NNNGGGGCTC CATGGGGNNN                                                     20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: one-of(1, 2, 18)
        (D) OTHER INFORMATION: /note= "N is G modified by thioxo."

(ix) FEATURE:
        (A) NAME/KEY: misc_feature
        (B) LOCATION: 3
        (D) OTHER INFORMATION: /note= "N is C modified by thioxo."

(ix) FEATURE:
        (A) NAME/KEY: misc_feature
        (B) LOCATION: 19
        (D) OTHER INFORMATION: /note= "N is T modified by thioxo."

(ix) FEATURE:
        (A) NAME/KEY: modified_base
        (B) LOCATION: 20
        (D) OTHER INFORMATION: /note= "N is C modified by
            p-OC-14."

(xi) SEQUENCE DESCRIPTION: SEQ ID NO:23:

NNNGGGGCTC CATGGGGNNN                                                     20

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: one-of(1, 19, 20)
        (D) OTHER INFORMATION: /note= "N is G modified by thioxo."

(ix) FEATURE:
        (A) NAME/KEY: misc_feature
        (B) LOCATION: 2
        (D) OTHER INFORMATION: /note= "N is C modified by thioxo."

(ix) FEATURE:
        (A) NAME/KEY: misc_feature
        (B) LOCATION: 18
        (D) OTHER INFORMATION: /note= "N is A modified by thioxo."

(ix) FEATURE:
        (A) NAME/KEY: modified_base
        (B) LOCATION: 21
        (D) OTHER INFORMATION: /note= "N is C modified by OH."

(xi) SEQUENCE DESCRIPTION: SEQ ID NO:24:

NNAGGAGGAT GCTGAGGNNN N                                                   21

(2) INFORMATION FOR SEQ ID NO:25:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: one-of(1, 19, 20)
        (D) OTHER INFORMATION: /note= "N is G modified by thioxo."

(ix) FEATURE:
        (A) NAME/KEY: misc_feature
        (B) LOCATION: 2
        (D) OTHER INFORMATION: /note= "N is C modified by thioxo."

(ix) FEATURE:
        (A) NAME/KEY: misc_feature
        (B) LOCATION: 18
        (D) OTHER INFORMATION: /note= "N is A modified by thoixo."

(ix) FEATURE:
        (A) NAME/KEY: modified_base
        (B) LOCATION: 21
        (D) OTHER INFORMATION: /note= "N is C modified by p-OC-12."

(xi) SEQUENCE DESCRIPTION: SEQ ID NO:25:

NNAGGAGGAT GCTGAGGNNN N                                           21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: one-of(1, 19, 20)
        (D) OTHER INFORMATION: /note= "N is G modified by thioxo."

(ix) FEATURE:
        (A) NAME/KEY: misc_feature
        (B) LOCATION: 2
        (D) OTHER INFORMATION: /note= "N is C modified by thioxo."

(ix) FEATURE:
        (A) NAME/KEY: misc_feature
        (B) LOCATION: 18
        (C) OTHER INFORMATION: /note= "N is A modified by thioxo."

(ix) FEATURE:
        (A) NAME/KEY: modified_base
        (B) LOCATION: 21
        (D) OTHER INFORMATION: /note= "N is C modified by
            p-OC-14."

(xi) SEQUENCE DESCRIPTION: SEQ ID NO:26:

NNAGGAGGAT GCTGAGGNNN N                                           21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: one-of(1, 19, 20)
```

(D) OTHER INFORMATION: /note= "N is G modified by thioxo."

(ix) FEATURE:
            (A) NAME/KEY: misc_feature
            (B) LOCATION: 2
            (D) OTHER INFORMATION: /note= "N is C modified by thioxo."

(ix) FEATURE:
            (A) NAME/KEY: misc_feature
            (B) LOCATION: 18
            (D) OTHER INFORMATION: /note= "N is A modified by thioxo."

(ix) FEATURE:
            (A) NAME/KEY: modified_base
            (B) LOCATION: 21
            (D) OTHER INFORMATION: /note= "N is C modified by
                p-OC-16."

(xi) SEQUENCE DESCRIPTION: SEQ ID NO:27:

NNAGGAGGAT GCTGAGGNNN N                                            21

(2) INFORMATION FOR SEQ ID NO:28:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (ix) FEATURE:
            (A) NAME/KEY: misc_feature
            (B) LOCATION: one-of(1, 19, 20)
            (D) OTHER INFORMATION: /note= "N is G modified by thioxo."

(ix) FEATURE:
            (A) NAME/KEY: misc_feature
            (B) LOCATION: 2
            (D) OTHER INFORMATION: /note= "N is C modified by thioxo."

(ix) FEATURE:
            (A) NAME/KEY: misc_feature
            (B) LOCATION: 18
            (D) OTHER INFORMATION: /note= "N is A modified by thioxo."

(ix) FEATURE:
            (A) NAME/KEY: modified_base
            (B) LOCATION: 21
            (D) OTHER INFORMATION: /note= "N is C modified by
                p-OC-18."

(xi) SEQUENCE DESCRIPTION: SEQ ID NO:28:

NNAGGAGGAT GCTGAGGNNN N                                            21

(2) INFORMATION FOR SEQ ID NO:29:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (ix) FEATURE:
            (A) NAME/KEY: misc_feature
            (B) LOCATION: one-of(1, 2, 20)
            (D) OTHER INFORMATION: /note= "N is C modified by thioxo."

(ix) FEATURE:
            (A) NAME/KEY: misc_feature
            (B) LOCATION: one-of(18, 19)
            (D) OTHER INFORMATION: /note= "N is G modified by thioxo."

```
    (ix) FEATURE:
         (A) NAME/KEY: modified_base
         (B) LOCATION: 21
         (D) OTHER INFORMATION: /note= "N is C modified by
             p-OC-14."

(xi) SEQUENCE DESCRIPTION: SEQ ID NO:29:

NNAGGGTACA GGTGGCCNNN N                                                 21

(2) INFORMATION FOR SEQ ID NO:30:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: Other nucleic acid (ix) FEATURE:
         (A) NAME/KEY: misc_feature
         (B) LOCATION: one-of(1, 2, 20)
         (D) OTHER INFORMATION: /note= "N is C modified by thioxo."

(ix) FEATURE:
         (A) NAME/KEY: misc_feature
         (B) LOCATION: one-of(18, 19)
         (D) OTHER INFORMATION: /note= "N is G modified by thioxo."

(ix) FEATURE:
         (A) NAME/KEY: modified_base
         (B) LOCATION: 21
         (D) OTHER INFORMATION: /note= "N is C modified by OH."

(xi) SEQUENCE DESCRIPTION: SEQ ID NO:30:

NNAGGGTACA GGTGGCCNNN N                                                 21

(2) INFORMATION FOR SEQ ID NO:31:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: Other nucleic acid (ix) FEATURE:
         (A) NAME/KEY: misc_feature
         (B) LOCATION: one-of(1, 2, 20)
         (D) OTHER INFORMATION: /note= "N is C modified by thioxo."

(ix) FEATURE:
         (A) NAME/KEY: misc_feature
         (B) LOCATION: one-of(18, 19)
         (D) OTHER INFORMATION: /note= "N is G modified by thioxo."

(ix) FEATURE:
         (A) NAME/KEY: modified_base
         (B) LOCATION: 21
         (D) OTHER INFORMATION: /note= "N is C modified by
             p-OC-16."

(xi) SEQUENCE DESCRIPTION: SEQ ID NO:31:

NNAGGGTACA GGTGGCCNNN N                                                 21
```

OLIGONUCLEOTIDE ANALOGS, THEIR PREPARATION AND USE

This application is a Continuation-in-Part of application U.S. Ser. No. 08/003,972, filed Jan. 19, 1993, now abandoned.

The present invention relates to novel oligonucleotide analogs with useful physical, biological and pharmacological properties and a process for their preparation. They can be used as inhibitors of gene expression (antisense oligonucleotides, ribozymes, sense oligonucleotides and triplex-forming oligonucleotides), as probes for detecting nucleic acids, and as aids in molecular biology. Oligonucleotides are being used to an increasing extent as inhibitors of gene expression (G. Zon, Pharmaceutical Research 5:539 (1988); J. S. Cohen, Topics in Molecular and Structural Biology 12 (1989) Macmillan Press; C. Helene and J. J. Toulme, Biochimica et Biophysica Acta 1049:99 (1990); Offensperger et al., The EMBO Journal 12:1257–1262 (1993); E. Uhlmann and A. Peyman, Chemical Reviews 90:543 (1990)).

The above-cited article of Uhlmann et al. discloses oligonucleotide conjugates linked via the 5' end and oligonucleotides linked via the 3' end and a process for their preparation (pp. 558–561). With regard to oligonucleotides described in the article, it is mentioned that modified, nuclease-resistant oligos, i.e., phosphorothioate oligos, may be degraded in a host (p. 566), that phosphorothioate oligos may have a lesser affinity for their target sequences (p. 562, right column, second paragraph; p. 564, first full paragraph), that phosphorothioate oligos do not penetrate cells as well as unmodified oligos (p. 568, left column, second full paragraph), that the distribution of the oligonucleotide analogues through an organism is non-uniform, with the pattern of distribution dependent on the type of oligo, i.e., its modification and length, and the target RNA or DNA (p. 568, right column), and that some phosphorothioate oligos show in general a less specific activity than methylphosphonate oligonucleotides (p. 565, left column, first paragraph).

Antisense oligonucleotides are nucleic acid fragments whose base sequence is complementary to an mRNA which is to be inhibited. This target mRNA can be of cellular, viral or other pathogenic origin. Suitable cellular target sequences are, for example, those of receptors, enzymes, immunomodulators, ion channels or oncogenes. The inhibition of viral replication using antisense oligonucleotides has been described, for example, for RSV (Rous sarcoma virus), HSV-1 and -2 (herpes simplex virus type I and II), HIV (human immunodeficiency virus) and influenza viruses. In this context, oligonucleotides are employed which are complementary to the viral nucleic acid. By contrast, the sequences of sense oligonucleotides are designed in such a way that these oligonucleotides bind ("capture") nucleic acid-binding proteins or nucleic acid-processing enzymes, for example, and thereby inhibit their biological activity (Helene, 1990). Viral targets which can be mentioned here as examples are reverse transcriptase, DNA polymerase and transactivator proteins. Triplex-forming oligonucleotides generally have DNA as their target, and after binding to this DNA form a triple helical structure. While generally the processing (splicing etc.) of mRNA and its translation into protein are inhibited using antisense oligonucleotides, triplex-forming oligonucleotides inhibit the transcription or replication of DNA (Helene et al., 1990, Uhlmann and Peyman, 1990). However, it is also possible to bind single-stranded nucleic acids in a first hybridization with an antisense oligonucleotide, with the formation of a double strand which then forms a triplex structure with a triplex-forming oligonucleotide in a second hybridization. In this case, the antisense and triplex binding regions can be contained either in two separate oligonucleotides or in one oligonucleotide. The so-called ribozymes, which destroy the target RNA as a result of their ribonuclease activity (J. J. Rossi and N. Sarver, TIBTECH 8:179 (1990)), represent a further application of synthetic oligonucleotides.

Suitably labeled nucleic acid fragments are employed in DNA diagnostic investigation as so-called DNA probes for specific hybridization to a nucleic acid which is to be detected. Here, the specific formation of the new double strand is followed using labeling which preferably is not radioactive. In this way, genetic and malignant diseases, and diseases caused by viruses or other pathogens, can be detected.

In their naturally occurring form, oligonucleotides are little, or not at all, suited for the majority of the said applications. They have to be chemically modified so that they are suitable for the specific requirements. In order that oligonucleotides can be employed in biological systems, for example for inhibition of viral replication, they must fulfil the following preconditions:

1. They must possess a sufficiently high degree of stability under in vivo conditions, in serum as well as intracellularly.
2. They must be able to pass through the cell and nuclear membranes.
3. They must bind to their target nucleic acid in a base-specific manner under physiological conditions in order to exert the inhibitory effect.

These preconditions are not essential for DNA probes; however, these oligonucleotides must be derivatized in a manner which permits detection, for example, by fluorescence, chemiluminescence, colorimetry or specific staining, (Beck and Köster, Anal. Chem. 62:2258 (1990)).

Chemical alteration of the oligonucleotides usually takes place by altering the phosphate backbone, the ribose unit or the nucleotide bases in an appropriate manner (Cohen, 1989; Uhlmann and Peyman, 1990). A further method, which is frequently employed, is the preparation of oligonucleotide 5'-conjugates by reacting the 5'-hydroxyl group with appropriate phosphorylation reagents. Oligonucleotides which are only modified at the 5'-end have the disadvantage that they are degraded in serum. If, on the other hand, all the internucleotide phosphate radicals are altered, the properties of the oligonucleotides are often drastically changed. For example, the solubility of the methylphosphonate oligonucleotides in aqueous medium is diminished, as is their ability to hybridize. Phosphorothioate oligonucleotides have nonspecific effects, so that, for example, homooligomers are also active against viruses.

The object is, therefore, to prepare oligonucleotide analogs with specific activity, increased serum stability, and good solubility.

The invention relates to oligonucleotide analogs of the formula I $$\text{(I)}$$

[Structural formula showing: $R^1-V$ connected to a sugar ring with Q, B, Y, $R^2$ substituents; $U-P(=W)-V$ linkage; repeated n times; terminating in another sugar ring with Q, B, Y', $R^2$; then $Z-P(=W)-X$]

and their physiologically tolerated salts, where $R^1$ is hydrogen, $C_1$–$C_{18}$-alkyl, preferably $C_1$–$C_6$-alkyl, $C_2$–$C_{18}$-alkenyl, $C_2$–$C_{18}$alkynyl, $C_2$–$C_{18}$ alkylcarbonyl, $C_3$–$C_{19}$-alkenylcarbonyl, $C_3$–$C_{19}$-alkynylcarbonyl, $C_6$–$C_{20}$-aryl, ($C_6$–$C_{14}$)-aryl-($C_1$–$C_8$)-alkyl, or a radical of the formula II $$Z-\underset{\underset{W}{\|}}{P}-Z';\quad\text{(II)}$$

$R^2$ is hydrogen, hydroxyl, $C_1$–$C_{18}$-alkoxy, halogen, azido, or $NH_2$;

B is a conventional base in nucleotide chemistry, e.g., natural bases such as adenine, cytosine, guanine, and thymine or unnatural bases such as purine, 2,6-diaminopurine, 7-deazaadenine, 7-deazaguanine, $N^4N^4$-ethanocytosine, $N^4N^4$-ethano-2,6-diaminopurine, pseudoisocytosine;

a is oxy or methylene;

n is an integer from 1 to 100, preferably 10 to 40;

W is oxo, thioxo, or selenoxo;

V is oxy, thio, or imino;

Y is oxy, thio, imino, or methylene;

Y' is oxy, thio, imino, $(CH_2)_m$, or $V(CH_2)_m$ where m is an integer from 1 to 18, preferably from l to 6;

X is hydroxyl or mercapto;

U is hydroxyl, mercapto, SeH, $C_1$–$C_{18}$-alkoxy, preferably $C_1$–$C_6$-alkoxy, $C_1$–$C_{18}$-alkyl, preferably $C_1$–$C_6$-alkyl, $C_6$–$C_{20}$-aryl, $C_6$–$C_{20}$-aryloxy, ($C_6$–$C_{14}$)-aryl-($C_1$–$C_8$)-alkyl, $NHR^3$, $NR^3R^4$, or a radical of the formula III $(OCH_2CH_2)_pO(CH_2)_qCH_2R^{11}$ (III), where $R^3$ is $C_1$–$C_{18}$-alkyl, preferably $C_1$–$C_8$-alkyl, $C_6$–$C_{20}$-aryl, ($C_6$–$C_{14}$)-aryl-($C_1C_8$)-alkyl, —$(CH_2)_c$—$[NH(CH_2)_c]_d$—$NR^{12}R^{12}$, where c is an integer from 2 to 6 and d is an integer from 0 to 6, and each $R^{12}$ independently of the other is hydrogen or $C_1$–$C_6$-alkyl or $C_1$–$C_4$-alkoxy-$C_1$–$C_6$-alkyl, preferably methoxyethyl;

$R^4$ is $C_1$–$C_{18}$-alkyl, preferably $C_1$–$C_8$-alkyl and particularly preferably $C_1$–$C_4$-alkyl, $C_6$–$C_{20}$-aryl or ($C_6$–$C_{10}$)-aryl-($C_1$–$C_8$)-alkyl, or, in the case of $NR^3R^4$, is, together with $R^3$ and the nitrogen atom carrying them, a 5–6-membered heterocyclic ring, which can additionally contain a further hetero atom selected from the group comprising O, S, N, p is an integer from 1 to 100, preferably 3 to 20 and particularly preferably 3 to 8, q is an integer from 0 to 22, preferably 0 to 15, $R^{11}$ is hydrogen or a functional group such as hydroxyl, amino, $NHR^{13}$, COOH, $CONH_2$, $COOR^{12}$, or halogen, where $R^{12}$ is $C_1$–$C_{14}$-alkyl, preferably methyl;

Z=Z' are hydroxyl; mercapto; SeH; $C_1$–$C_{22}$-alkoxy, preferably $C_6$–$C_{18}$-alkoxy, —O—$(CH_2)_b$—$NR^{12}R^{13}$, where b is an integer from 1 to 6, and $R^{13}$ is $C_1$–$C_6$-alkyl or $R^{12}$ and $R^{13}$ together with the nitrogen atom carrying them, form a 3–6-membered ring; $C_1$–$C_{18}$-alkyl, preferably $C_1$–$C_8$-alkyl, $C_6$–$C_{20}$-aryl; ($C_6$–$C_{14}$)-aryl-($C_1$–$C_8$)-alkyl, preferably ($C_6$–$C_{10}$)-aryl-($C_1$–$C_4$)-alkyl; ($C_6$–$C_{14}$)-aryl-($C_1$–$C_8$)-alkoxy, preferably ($C_6$–$C_{10}$)-aryl-($C_1$–$C_4$)-alkoxy, where aryl includes heteroaryl, and aryl is optionally substituted by 1, 2, or 3 identical or different radicals selected from the group comprising carboxyl, amino, nitro, $C_1$–$C_4$-alkylamino, $C_1$–$C_6$-alkoxy, hydroxyl, halogen, and cyano; $C_1$–$C_{18}$-alkyl-mercapto; $NHR^3$, $NR^3R^4$; a radical of the formula III; or a group which favors intracellular uptake or serves as the label for a DNA probe, or, during hybridization of the oligonucleotide analog to the target nucleic acid, attacks the latter with binding, crosslinking or cleavage, and the curved bracket indicates that $R^2$ and the neighboring phosphoryl residue can be located in the 2'- and 3'-position or else the opposite way in the 3'- and 2'-position, where each nucleotide can be present in its D- or L-configuration and the base B can be located in the α- or β-position, with the proviso that, if Z=hydroxyl, mercapto, methyl, or ethoxy, at least one of the groups X, Y, Y', V, and W is not hydroxyl, oxy, or oxo, or R' is not hydrogen.

Preferred are oligonucleotide analogs of the formula I and their physiologically tolerated salts, where base B is located in the β-position, the nucleotides are present in the D-configuration, $R^2$ is located in the 2'-position, and a is oxy.

Particularly preferred are oligonucleotide analogs of the formula I, where $R^1$ is hydrogen, $C_1$–$C_6$-alkyl, in particular methyl, or a radical of the formula II;

$R^2$ is hydrogen or hydroxyl, in particular hydrogen;

n is an integer from 10 to 40, in particular 12 to 30;

m is an integer from 1 to 6, in particular 1;

U is hydroxyl, mercapto, $C_1$–$C_6$-alkoxy, $C_1$–$C_6$-alkyl, $NR^3R^4$, or $NHR^3$, in particular hydroxyl or $C_1$–$C_6$-alkyl, where $R^3$ is $C_1$–$C_8$-alkyl, preferably $C_1$–$C_4$-alkyl, or methoxyethyl, and B, W, V, Y, Y', X, and Z have the above-mentioned meaning.

Especially preferred are oligonucleotide analogs of the formula I, where V, Y', and Y have the meaning of oxy. Additionally particularly preferred are oligonucleotide analogs of the formula I, where V, Y, Y', and W have the meaning of oxy or oxo.

Very particularly preferred are oligonucleotide analogs of the formula I, where V, Y, Y', W, and U have the meaning of oxy, oxo, or hydroxyl.

Furthermore, oligonucleotide analogs of the formula I are preferred, where $R^1$ is hydrogen.

Especially preferred are oligonucleotide analogs of the formula I, where U, V, W, X, Y', and Y have the meaning of oxy, oxo, or hydroxyl and $R^1$ is hydrogen.

The residues which occur repeatedly, such as $R^2$, B, a, W, V, Y, U, $R^3$, $R^4$, p, q, and Z, can, independently of each other, have identical or different meanings, i.e., each V, for example, is, independently of the others, oxy, thio, or imino.

Halogen is preferably fluorine, chlorine, or bromine. Heteroaryl is understood to mean the radical of a monocyclic or bicyclic ($C_3$–$C_9$)-heteroaromatic, which contains one or two N atoms and/or an S or an O atom in the ring system.

Examples of groups which favor intercellular uptake are various lipophilic radicals such as —O—$(CH_2)_x$—$CH_3$, where x is an integer from 6–18, —O—$(CH_2)_n$—CH=CH—$(CH_2)_m$—$CH_3$, where n and m are independently of each other an integer from 6 to 12, —O—$(CH_2CH_2O)_4$—$(CH_2)_9$—$CH_3$, —O—$(CH_2CH_2O)_8$—$(CH_2)_{13}$—$CH_3$ and —O—$(CH_2CH_2O)_7$—$(CH_2)_{15}$—$CH_3$, and also steroid residues, such as cholesteryl, and conjugates which make use of natural carrier systems, such as bile acid, folic acid, 2-(N-alkyl, N-alkoxy)-aminoanthraquinone, and conjugates of mannose and peptides of the corresponding receptors, which lead to receptor-mediated endocytosis of the oligonucleotides, such as EGF (epidermal growth factor), bradykinin, and PDGF (platelet derived growth factor).

Labeling groups are understood to mean fluorescent groups, for example, dansyl (=N-dimethyl-1-aminonaphthyl-5-sulfonyl) derivatives, fluorescein derivatives or coumarin derivatives, or chemiluminescent groups, for example, acridine derivatives, as well as the digoxigenin system, which is detectable by ELISA, the biotin group, which is detectable by the biotin/avidin system, or linker arms with functional groups which allow a subsequent derivatization with detectable reporter groups, for example, an aminoalkyl linker, which is reacted with an acridinium active ester to form the chemiluminescent probe.

Typical labeling groups are:

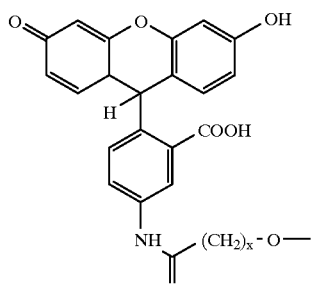

Fluorescein derivative
(x = 2–18, preferably 4–6)

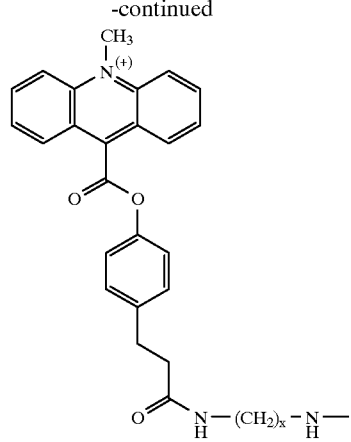

Acridinium ester

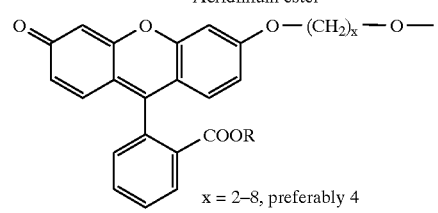

x = 2–8, preferably 4
R = H or $C_1$-$C_4$ — alkyl
(= "fluorescein" for x = 4 and R = $CH_3$)

Fluorescein derivative
R = H or amino-protective group

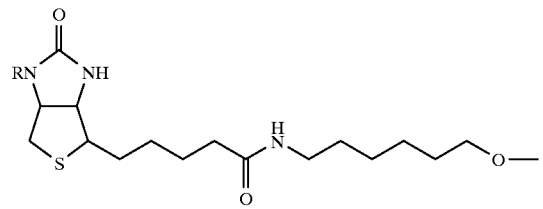

Bitoin conjugate (= "biotin" for R = Fmoc)

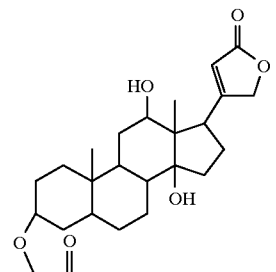

Dioxigenin conjugate

Oligonucleotide analogs which bind to nucleic acids or intercalate and/or cleave or crosslink contain, for example, acridine, psoralen, phenanthridine, naphthoquinone, daunomycin, or chloroethylaminoaryl conjugates. Typical intercalating and crosslinking residues are:

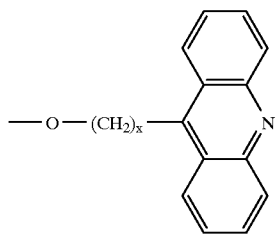

Acridine derivative x = 2–12, preferably 4

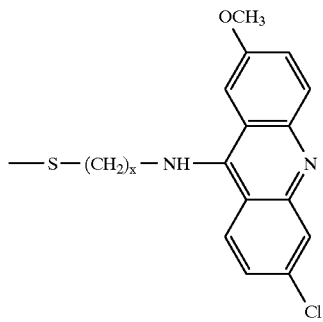

x = 2–12, preferably 4

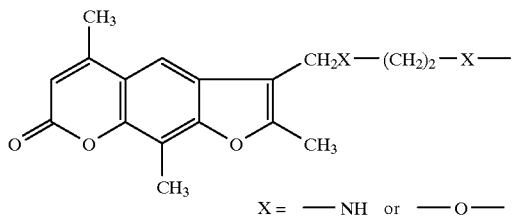

X = —NH— or —O—

Trimethylpsoralen conjugate (= "psoralen" for X = O)

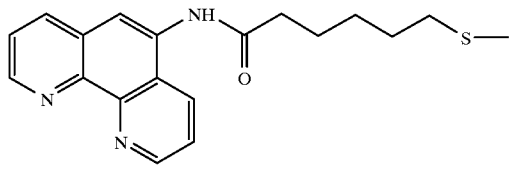

Phenanthroline conjugate

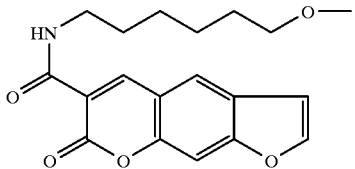

Psoralen conjugate

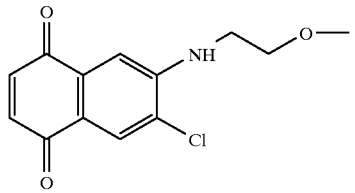

Naphthoquinone conjugate

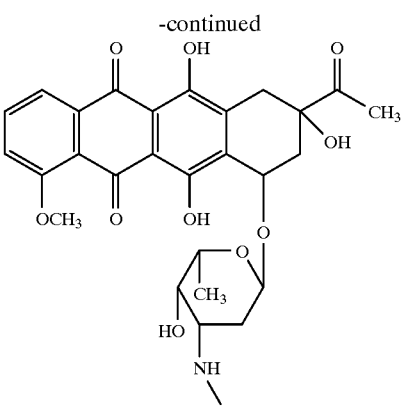

Daunomycin derivative

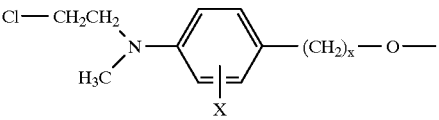

x = 1–18, X = alkyl, halogen, $NO_2$, CN, —C(=O)—R

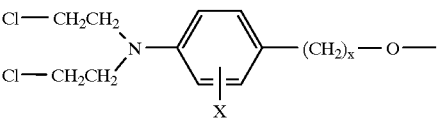

x = 1–18, X = alkyl, halogen, $NO_2$, CN, —C(=O)—R

The morpholinyl and the imidazolidinyl radicals may be mentioned as examples of $NR^3R^4$ groups in which $R^3$ and $R^4$, together with the nitrogen atom carrying them, form a 5- to 6-membered heterocyclic ring, which additionally contains a further hetero atom.

The invention is not limited to α- and β-D- or L-ribofuranosides, α- and β-D- or L-deoxyribofuranosides and corresponding carbocyclic 5-membered ring analogs, but is also valid for oligonucleotide analogs which are composed of other sugar components, for example ring-expanded and ring-contracted sugars, acyclic sugar derivatives or suitable sugar derivatives of another type. Furthermore, the invention is not limited to the derivatives of the phosphate radical which are cited by way of example in formula I, but also relates to the known dephosphorus derivatives.

As for the synthesis of biological oligonucleotides, the preparation of oligonucleotide analogs of the formula I takes place in solution or preferably on a solid phase, optionally with the aid of an automatic synthesis apparatus.

However, solid phase synthesis of oligonucleotides with a phosphate or phosphate ester radical at the 3'-end is not possible by the standard phosphoramidite chemistry of Caruthers (M. D. Matteucci and M. H. Caruthers, J. Am. Chem. Soc. 103:3185 (1981)), since the first nucleotide unit is bound to the solid support via the 3'-hydroxyl group and for this reason oligonucleotides with a 3'-hydroxyl group always result from these syntheses. Various processes based on the solid-phase method have been described, which processes, however, are all laborious and often cannot be used for preparing derivatives such as phosphate esters or alkylphosphonates (R. Eritja et al., Tetrahedron Lett. 32:1511 (1991); P. Kumar et al., Tetrahedron Lett. 32:967 (1991); W. T. Markiewicz and T. K. Wyrzykiewicz, Phosphorus, Sulfur and Silicon 51/52:374 (1990); E. Felder et al., Tetrahedron Lett. 25:3967 (1984); R. Lohrmann and J. Ruth, DNA 3:122 (1984)).

The invention therefore relates to a process for preparing oligonucleotide analogs of the formula I, where a) a nucleotide unit with a 3'(2')-terminal phosphorus-(V) grouping and a free 5'-hydroxyl or mercapto group is reacted with another nucleotide unit with a phosphorus (III) or phosphorus(V) grouping in the 3' position and a temporarily protected 5'-hydroxyl or mercapto group, or their activated derivatives, or b) the oligonucleotide analog is constructed with fragments in a similar manner, and protective groups, which have been temporarily introduced in the oligonucleotides obtained according to (a) or (b) in order to protect other functions, are removed and the oligonucleotide analogs of the formula I, thus, obtained are, where appropriate, converted into their physiologically tolerated salt.

Employed as starting component for the solid-phase synthesis is a solid support of the formula IV and polyethylene glycol (POE), which is modified in the side chain by functional groups such as hydroxyl, amino, halogen, or COOH, D is a protective group which can be removed without cleaving the linker arm A and the X'—CH$_2$CH$_2$S(O)$_x$CH$_2$CH$_2$— radical (see Bioorg. Chem. 14:274–325 (1986)), such as 4-methoxytetrahydropyranyl and dimethoxytrityl, preferably dimethoxytrityl, x is an integer zero, 1 or 2 and X' is oxy or thio.

The linker arm A, which connects the solid support T to the sulfur-containing radical by a chemical bond (amide, ester, inter alia) (Damha et al., Nucleic Acids Res. 18:3813 (1990)), is preferably a succinic acid residue (O—C(O)—CH$_2$CH$_2$—C(O)—), an oxalic acid residue (O—C(O)—C(O)—), an alkylamine, preferably LCAA (long chain alkylamine), or polyethylene glycol. A succinic acid residue is particularly preferred. In particular cases, for example in combination with substituents which do not withstand lengthy treatment with ammonia, more labile linkers such as the oxalyl linker are advantageous. The preparation of solid supports of the formulae IV a–c is described in Example 1.

| Support | D | X' | x | A-T |
|---|---|---|---|---|
| IVa | DMTr | O | 2 | —O—C(=O)—(CH$_2$)$_2$—C(=O)—N(H)—(CH$_2$)$_3$—Si-CPG (OEt, OEt) |
| IVb | DMTr | O | 2 | —O—C(=O)—(CH$_2$)$_2$—C(=O)—N(H)-TentaGel |
| IVc | DMTr | O | 0 | —O—P(=O)(OCH$_2$—CH$_2$—CN)—O-TentaGel |

where

A is a linker arm, which, for example, is a residue of a dicarboxylic acid, a dial, an alkylamine, a dicarboxylic acid monoalkylamide, an acid amide, or a phosphate of the formula

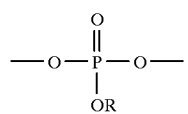

where R is equal to hydrogen or C$_1$–C$_6$-alkyl which is optionally substituted by —CN, preferably methyl or 2-cyanoethyl, T is a solid support, for example of materials such as CPG (controlled pore glass), silica gel or an organic resin such as polystyrene (PS) or a graft copolymer of PS The solid-phase synthesis can take place according to the phosphate triester method, the H-phosphonate method or the phosphoramidite method, preferably according to the phosphoramidite method (E. Sonveaux, Bioorg. Chem. 14:274 (1986)). The protective group D is always first of all removed from the support of the formula IV, preferably by an acid, for example, trichloroacetic acid in methylene chloride. In the case of the phosphoramidite method, the support of the formula IV' thus obtained

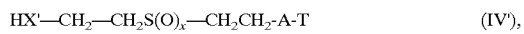

where x, X', A, and T have the above-mentioned meaning, is condensed in the presence of a weak acid such as tetrazole with a nucleoside phosphoramidite of the formula V

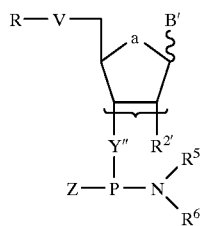

(V)

where
- R is a protective group which can be removed under mild conditions, such as 4-methoxytetrahydropyranyl or dimethoxytrityl,
- $R^2$ is hydrogen, $C_1$–$C_{18}$-alkoxy, halogen, or a protected hydroxyl or amino group and
- $R^5$ and $R^6$ independently of each other are $C_1$–$C_{12}$-alkyl, or both residues together form a 5 to 6-membered ring,
- Y" is oxy, thio, or $(CH_2)_m$, and
- a, m, V, and Z have the above-mentioned meaning.

Subsequently, the support thus obtained is oxidized in a manner known per se with iodine water (W=O) or with TETD (tetraethylthiuram disulfide) or elemental sulfur (W=S) or with selenium (W=Se) to form the derivatized support of the formula VII

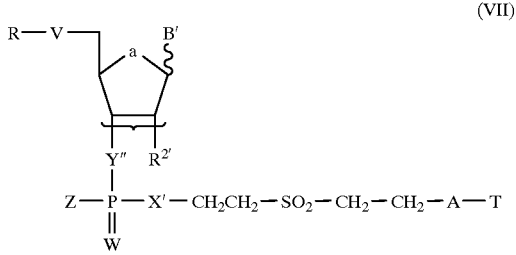

(VII)

where
R, V, B', $R^2$, Z, X', W, Y", A, and T have the above-mentioned meaning. Supports of the formula VIIa are preferably prepared.

The phosphoramidite of the formula V can be obtained, for example, from the bisamidite of the formula VI

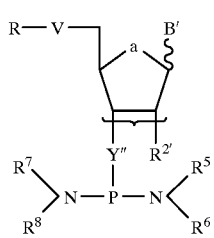

(VI)

where $R^7$ and $R^8$ are identical to $R^5$ and $R^6$ and a, R, V, B', $R^2$, Y", $R^5$, and $R^6$ have the above-mentioned meaning, by reaction with the corresponding alcohol or thioalcohol using tetrazole catalysis (Example 2, Method A), if Z is=alkoxy or alkylmercapto (J. E. Marugg et al., Tetrahedron Lett. 27:2271 (1986). Preferred bisamidites are those of the formula VIa

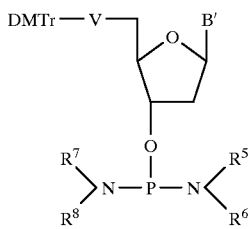

(VIa)

In this way the amidites of the formulae VIII a–m were prepared, for example,

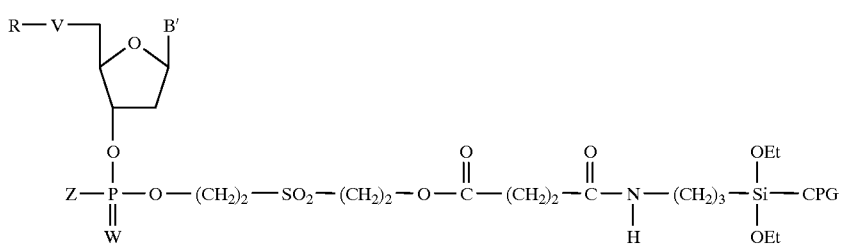

(VIIa)

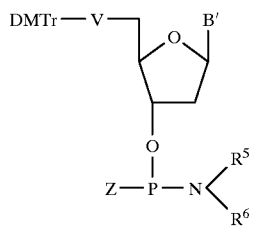
(VIII)

where
R[5] and R[6] have the above-mentioned meanings, Z has the meaning of
a) O—CH$_2$CH$_3$,
b) O-i-C$_3$H$_7$,
c) O-n-C$_6$H13
d) O-n-C$_{18}$H$_{37}$,
e)

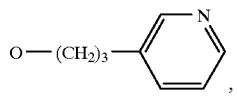

f)

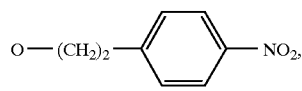

g) is a residue of the formula III (R[11]=H), wherein p=3 and q=0,
h) is a residue of the formula III (R[11]=H), wherein p=4 and q=9,
i) is a residue of the formula III (R[11]=H), wherein p=5 and q=4,
k) is a residue of the formula III (R[11]=H), wherein p=8 and q=13,
p) CH$_3$

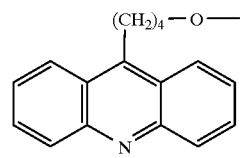

and B' is
Cyt$^{i\text{-}Bu}$ in the case of a), c) and d),
Thy in the case of b) and p) and
Cyt$^{Bz}$ in the case of e)–k) and m).

An alternative method for loading the support is the reaction of the phosphitylation reagent of the formula IX

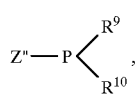
(IX)

where
R[9] and R[10] are, independently of each other, Cl, or Z", where Z" is=Z, with the proviso that hydroxyl, mercapto, and SeH must be present as protected derivatives,

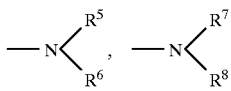

for example as O—CH$_2$CH$_2$—CN, O—CH$_3$, S—CH$_2$CH$_2$CN, X'—CH$_2$CH$_2$—S(O)$_x$, —CH$_2$CH$_2$—X'-D, or

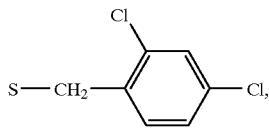

preferably as X'CH$_2$CH$_2$—S(O)$_x$, —CH$_2$CH$_2$—X'-DMTr, where x' is an integer zero or 1, in particular as O—CH$_2$CH$_2$—S—CH$_2$CH$_2$—O-DMTr, and R[5], R[6], R[7], R[8], X', DMTr, and D have the above-mentioned meaning, with a nucleoside with a free 3'(2')-group of the formula X

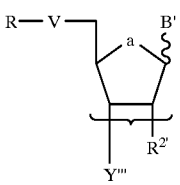
(X)

where
Y''' is oxy or thio and V, B', and R have the above-mentioned meaning, and subsequent condensation of the compound thus obtained onto the support of the formula IV' in the presence of a condensing agent, such as tetrazole (for R[9], R[10]=NR[5]R[6] or NR[7]R[8]) or diisopropylamine (for R[9], R[10]=Cl); this often represents the quicker method (Example 3, method B). Subsequent oxidation with iodine water or sulfur or selenium then leads to the compound of the formula VIIa. The protective group R can now be removed and the oligonucleotide synthesis continued in a known manner. At the end of the synthesis, the protective groups are removed in a known manner from the support-bound oligonucleotide analog thus obtained, and the oligonucleotide analog of the formula I according to the invention is then cleaved off the support. If the synthesis was concluded in the last cycle with a unit of the formula V, an oligonucleotide analog of the formula I (R[1]=H) is obtained with a 5'-hydroxyl group and a phosphorus-containing conjugation at the 3'-end. If, on the other hand, a phosphorylating reagent, for example of the formula IX, where R[9] is=Z", is employed in the last condensation step, an oligonucleotide analog of the formula I with R[1]=formula II, which possesses a phosphate-containing substitution at both the 3'- and 5'-ends, then results from the synthesis.

The preparation of oligonucleotides with a 3'-terminal phosphoramidate group is, for example, possible by reaction of the support of the formula IV' (x=0) with the monomeric methoxyphosphoramidite of the formula V (Z=O—CH$_3$) in the presence of tetrazole, if the oxidation is carried out, as described in Jäeger et al. (Biochemistry 27:7237 (1988)), with iodine/$H_2NR^3$ or $HNR^3R^4$, where $R^3$ and $R^4$ have the above-mentioned meaning.

In certain cases ($Z=NHR^3$, $NR^3R^4$, O, S, or Se) the introduction of the group Z can also take place by the H-phosphonate method, in which a nucleoside H-phosphonate of the formula XI

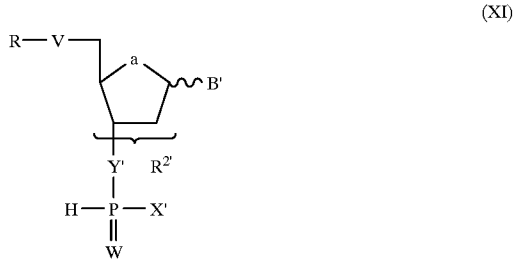

(XI)

where R, V, a, B', Y', X', and W have the above-mentioned meaning, is initially reacted with a support of the formula IV' in the presence of a condensing agent such as pivaloyl or adamantoyl chloride and a base such as pyridine. The H-phosphonate diester formed, of the formula VII'

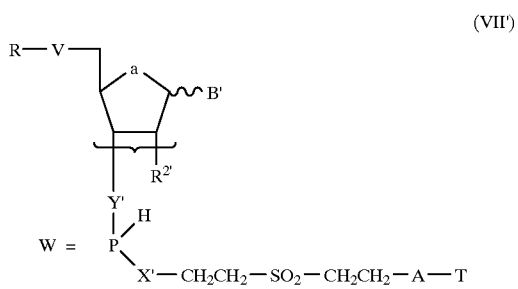

(VII')

is then subjected to an oxidative phosphoramidation (B. Froehler, Tetrahedron Lett. 27:5575 (1986)) or to oxidation with iodine water, sulfur, or selenium. In this way an oligonucleotide with a 3'-terminal cholesteryl group can be prepared starting from, for example, VII' (x=0), with a cholesteryloxycarbonyl-aminoalkylamine in the presence of carbon tetrachloride. By oxidative amidation with 2-methoxyethylamine, oligonucleotides with a 3'-O-(2'-methoxyethyl)-phosphoramidate residue are obtained. Subsequent chain construction takes place in a known manner according to the phosphoramidite, H-phosphonate, or triester methods.

The preparation of oligonucleotide analogs of the formula I is also possible using the triester method, where the hydroxyl group of the support of the formula IV' is reacted with a protected phosphate diester of the formula XII

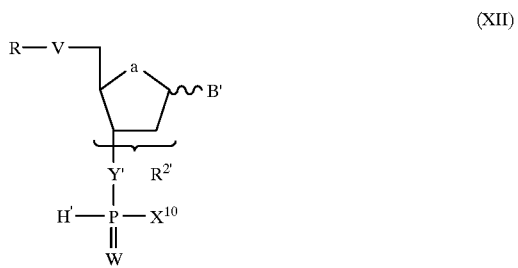

(XII)

where R, V, a, B', $R^2$, Y', Z, W, and X' have the above-mentioned meaning, in the presence of a condensing agent. Preferred condensation reagents are arylsulfonyl chlorides such as mesitylenesulfonyl chloride, 2,4,6-triisopropylbenzenesulfonyl chloride, or 8-quinolinesulfonyl chloride in the presence of nucleophilic catalysts such as imidazole, triazole, tetrazole, or their substituted derivatives such as N-methylimidazole, 3-nitrotriazole, or 5-(p-nitrophenyl)-tetrazole. Particularly preferred condensing agents are 4-substituted derivatives of pyridine-N-oxide or quinoline-N-oxide (Efimov et al., Nucleic Acids Research 13:3651 (1985)). Compared with the H-phosphonate and phosphoramidite processes, the triester process has the advantage that no additional oxidation step is required.

If the oligonucleotide synthesis is carried out with a thio (x=0) or sulfinyl (x=1) support of the formula IV', these groups are then at the end oxidized to the sulfonyl radical in a manner known per se (Funakoshi et al., Proc. Natl. Acad. Sci. 88:6982 (1991)), in order to ensure ready cleavage with bases, preferably ammonia.

The nature of the amino-protective groups of the bases B' and the constitution of the linker arm A depend, in the individual case, on the nature of the substituent Z, since the latter must be removable without difficulty once synthesis has been completed. For example, in preparing an oligonucleotide 3'-phosphate isopropyl ester ($Z=O-i-C_3H_7$), Benzoyl (Bz) protective groups can be used for B=Ade and Cyt and isobutyryl (i-Bu) protective groups for B=Gua. On the other hand, to synthesize an oligonucleotide 3'-methylphosphonate ester ($Z=CH_3$) or ethyl ester (Z=O—$C_2H_5$), the more labile phenoxyacetyl (PAC) and isobutyryl protective groups are used for B=Ade and Gua, and for B=Cyt, respectively.

Many conjugates possess additional functional groups, which must be protected in a suitable manner before incorporation into the monomeric units of the formula V. For example, the carboxyl group of fluorescein must be protected as an alkyl ester. In psoralen, the amide group can be present as a N-Fmoc (fluorenyl-methoxycarbonyl)-protected compound. Hydroxyl groups can be protected from side reactions by acylation or silylation (t-butyldimethylsilyl). Amino groups can also be present in the trifluoroacetyl-protected form. In exceptional cases, the conjugates may be so unstable that they would be decomposed under the conditions of protective-group removal during the oligonucleotide synthesis. In such cases it is convenient to incorporate only one linker arm with a functional group, for example, $Z=HN-(CH_2)_x-NH-Fmoc$, where x is an integer from 2–12, preferably 4–6, in the monomer of the formula V. After incorporation into the oligonucleotide and removal of the protective groups, preferably with ammonia, the free amino group may be coupled to active esters. The base-labile acridinium ester, for example, was prepared in this way.

Characterization of the synthesized oligonucleotide derivatives takes place by electro-spray ionization mass spectrometry (Stults and Masters, Rapid Commun. Mass. Spectr. 5:350 (1991)).

The oligonucleotide analogs of the formula I according to the invention were tested for their stability in serum and toward known exonucleases.

It was found, surprisingly, that, in comparison with the unmodified oligonucleotides, all oligonucleotide analogs of the formula I possess markedly increased stability toward the serum nucleases, while their hybridization behavior is only slightly affected.

While unmodified oligonucleotides have a half life of about two hours in fetal calf serum, all oligonucleotide analogs of the formula I are satisfactorily stable for about 16 hours. In addition, the oligonucleotide analogs of the formula I are stable toward snake venom phosphodiesterase, whereas only those where $R^1$ is not hydrogen are resistant to spleen phosphodiesterase. Unmodified oligonucleotides are degraded exonucleolytically from the 3'-end by snake venom phosphodiesterase and from the 5'-end by spleen phosphodiesterase.

With complementary single-stranded nucleotide sequences, the oligonucleotide analogs of the formula I form stable, double-stranded hybrids due to Watson-Crick base pairing, while they form triple helical structures with double-stranded nucleic acids due to Hoogsteen base pairing. In this way, the regulation or suppression of biological functions of nucleic acids is possible using the oligonucleotide analogs according to the invention, for example, suppression of the expression of cellular genes, as well as of oncogenes, or of viral genome functions. Oligonucleotide analogs of the formula I may, therefore, be used as medicaments for the therapy or prophylaxis of viral infections or cancers.

The activity of the oligonucleotides according to the invention was determined on the basis of the inhibition of HSV-1 viral replication. By way of example, the following oligonucleotides of the formula 1 were found to be active against HSV-1:

An oligonucleotide of the formula I modified with psoralen at the 3'-end (Example 4s) recognizes the IE4/5 region of HSV-2 and inhibits the replication of HSV-2. The antiviral activity of the psoralen conjugates may be significantly increased by irradiation with UV light. The HSV-1/2 genome, with its 160,000 bases, naturally offers innumerable alternative target sequences of diverse efficiency for inhibiting viral replication. By varying the nucleotide sequences, the therapeutic principle may be applied to any other viruses, bacteria or other pathogens. The sole prerequisite for transfer to other life cycle of these pathogens are known. The sequences of these genes are deposited in great variety in the so-called gene databases. This is also the case for oncogenes and other cellular genes whose function is to be suppressed. Examples of other cellular genes are those which encode enzymes, receptors, ion channels, immunomodulators, growth factors, and other regulatory proteins. Examples of oncogenes are abl, neu, myc, myb, ras, fos, mos, erbB, ets, jun, p53, src, and rel.

Antisense and triplex-forming oligonucleotide sequences are, for example, known as inhibitors of the cyclic AMP-

| Sequence HSV-1 | | Points of attack in |
|---|---|---|
| 5' GGG GCG GGG CTC CAT GGG GG | (SEQ ID NO:1) | IE 110 (start) |
| 5' CCG GAA AAC ATC GCG GTT GT | (SEQ ID NO:2) | UL30 (middle) |
| 5' GGT GCT GGT GCT GGA CGA CA | (SEQ ID NO:3) | UL48 (middle) |
| 5' GGC CCT GCT GTT CCG TGG CG | (SEQ ID NO:4) | UL52 (middle) |
| 5' CGT CCA TGT CGG CAA ACA GCT | (SEQ ID NO:5) | UL48 (start) |
| 5' GAC GTT CCT CCT GCG GGA AG | (SEQ ID NO:6) | IE4/5 (splice site) |

In their natural form, i.e., without 3'-derivatization, the selected sequences are inactive toward HSV-1 in cell culture, probably since they are subject to rapid degradation in serum or have insufficient cell penetration. On the other hand, the 3'-derivatized oligonucleotides of the formula I inhibit HSV-1 replication to differing extents. The following served as control sequences with the appropriate chemical derivatization but with no antiviral activity:

5'CCA GGG TAC AGG TGG CCG GC (SEQ ID NO:7)   control

5'GAC TAA TCG GGA ATG TTA AG (SEQ ID NO:8)   control dependent protein kinase (L. Sheffield, Exp. Cell Res. 192:307 (1991)), the strychnine-sensitive glycine receptor (Akagi et al., Proc. Natl. Acad. Sci. U.S.A. 86:8103 (1989)), the chloride channel (Sorscher et al., Proc. Natl. Acad. Sci. U.S.A. 88:7759 (1991)), Interleukin-6 (Levy et al., J. Clin. Invest. 88:696 (1991)), the basic fibroblast growth factor (Becker et al., EMBO J. 8:3685 (1989)), and the c-myc oncogene (Postel et al., Proc. Natl. Acad. Sci. U.S.A. 88:8227 (1991)). The following further examples of sequences of other target molecules are intended to illustrate the broad applicability of the oligonucleotides according to the invention.

a) Antisense oligonucleotides against HIV-1:

5' ACA CCC AAT TCT GAA AAT GG 3' (SEQ ID NO:9) (splice site)

5' AGG TCC CTG TTC GGG CGC CA 3' (SEQ ID NO:10) (primer binding site)

-continued b) EGF receptor (epidermal growth factor receptor)

5' GGG ACT CCG GCG CAG CGC 3' (SEQ ID NO:11) (5' untranslated)

5' GGC AAA CTT TCT TTT CCT CC 3' (SEQ ID NO:12) (aminoterminal)

c) p53 tumor suppressor

5' GGG AAG GAG GAG GAT GAG G 3' (SEQ ID NO:13) (5'-noncoding)

5' GGC AGT CAT CCA GCT TCG GAG 3' (SEQ ID NO:14) (start of translation)

d) c-fos oncogene

5' CCC GAG AAC ATC ATG GTC GAA G 3' (SEQ ID NO:15) (start of translation)

5' GGG GAA AGC CCG GCA AGG GG 3' (SEQ ID NO:16) (5'-noncoding)

e) ELAM-1 (endothelial leucocyte adhesion molecule)

5' ACT GCT GCC TCT TGT CTC AGG 3' (SEQ ID NO:17) (5'-noncoding)

5' CAA TCA ATG ACT TCA AGA GTT C 3' (SEQ ID NO:18) (start of translation)

f) ICAM-1 (intracellular adhesion molecule)

5' CTC CCC CAC CAC TTC CCC TC 3' (SEQ ID NO:19) (3'untranslated)

5' GCT GGG AGC CAT AGC GAG G 3' (SEQ ID NO:20) (start of translation)

g) BCR-ABL (Philadelphia chromosome translocation)

GCT GAA GGG CTT CTT CCT TAT TG 3' (SEQ ID NO:21) (BCR-ABL breakpoint)

Compared to the oligonucleotide derivatives with a 3'-hydroxyl group, known from the literature, DNA probes which comprise oligonucleotide analogs of the formula I, on the one hand, offer the advantage of increased nuclease stability and, on the other, permit the acceptance of identical or different marker molecules at both ends of the oligonucleotide. It is advantageous that different marker groupings can be selectively activated within one oligonucleotide (double labeling). The bifunctional derivatization can also be used to introduce a label at the one end and an additional function (for example, an affinity label) at the other end. For this purpose, biotin, which recognizes avidin or streptavidin, can, for example, be incorporated at the 3'-end of the oligonucleotide, while an acridinium ester chemiluminescence label can be attached to the 5'-end via an alkylamino linker.

The evaluation of the biological activity of antisense oligonucleotides is explained here by means of the antiviral assay. However, their use is not limited to this indication because the antisense principle is of a general character. Evaluation of antisense compounds is usually done by testing them in cell culture which is a good measure for their activity in whole animal systems. Offensperger et al., The EMBO J. 12:1257–1262 (1993).

Although in the below-described Example 9, the oligonucleotide is administered intraperitoneally to mice, other types of application like intravenous, intranasal, topical, or catheter administration will work as well depending on the type of disease.

In addition, the penetration behavior of the oligonucleotide analogs according to the invention is in many cases more favorable than in the case of unmodified oligonucleotides, in particular, if lipophilic radicals are introduced. The increased stability of the oligonucleotides and their improved cell penetration are expressed in the form of a higher biological activity as compared with the unmodified oligonucleotides.

The previously mentioned diagnostic, prophylactic, and therapeutic applications of the oligonucleotide analogs according to the invention are only a selection of representative examples, and the use of the analogs is, therefore, not limited to them.

In addition, the oligonucleotide analogs according to the invention may, for example, be employed as aids in biotechnology and molecular biology.

The invention relates, furthermore, to pharmaceutical preparations which contain an effective amount of one or more compounds of the formula I or their physiologically tolerated salts, where appropriate, together with physiologically tolerated adjuvants and/or excipients, and/or other known active substances, as well as a process for preparing these preparations, wherein the active substance, together with the excipient and possibly further adjuvants, additives or active substances, is converted into a suitable presentation.

Administration preferably takes place intravenously, topically, or intranasally, but is not limited to these means, since the type of disease, the degree of infection, and other patient-specific factors will dictate the optimal means of administration. Thus, even one virus may cause different pathological phenotypes. For example, in case of a moderate herpes keratitis administration may be done in form of eye drops whereas in case of severe keratitis, direct injection of the compound into the eye may be necessary. In case of a herpes-induced meningitis, systemic administration will be required. Other targets like c-myc can be downregulated with antisense oligonucleotides in cell culture or in animals. Since c-myc is involved in cell proliferation, inhibition of c-myc can be applied to stop tumor growth. For this, local antisense oligonucleotide treatment of solid tumor is used. But if the tumor is spreading, systemic treatment (i.v. injection) is the method of choice. The same target can be inhibited to prevent restenosis after coronary balloon angioplasty. In this case, the c-myc antisense oligonucleotide (which was also used to prevent tumor growth) will be administered via a catheter to the affected vessel in a relatively small amount (about 1 mg per dose and patient) as compared to cancer treatment. In summary, it can be stated that the type of administration, the amount of drug applied and the adjustment of similar parameters can be handled, accordingly, by someone of ordinary skill in the art.

Figure 1:
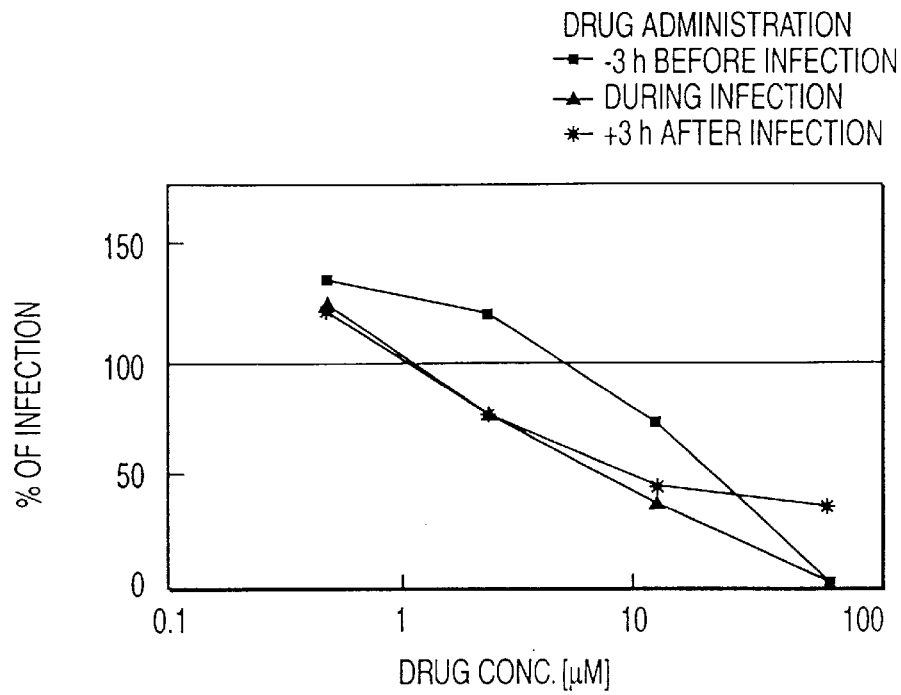
FIG. 1 shows the results of a single cycle experiment demonstrating the antiviral activity of Herp 18c (SEQ ID NO:27) against HSV-1 (multiplicity of infection=10).
Figure 2:
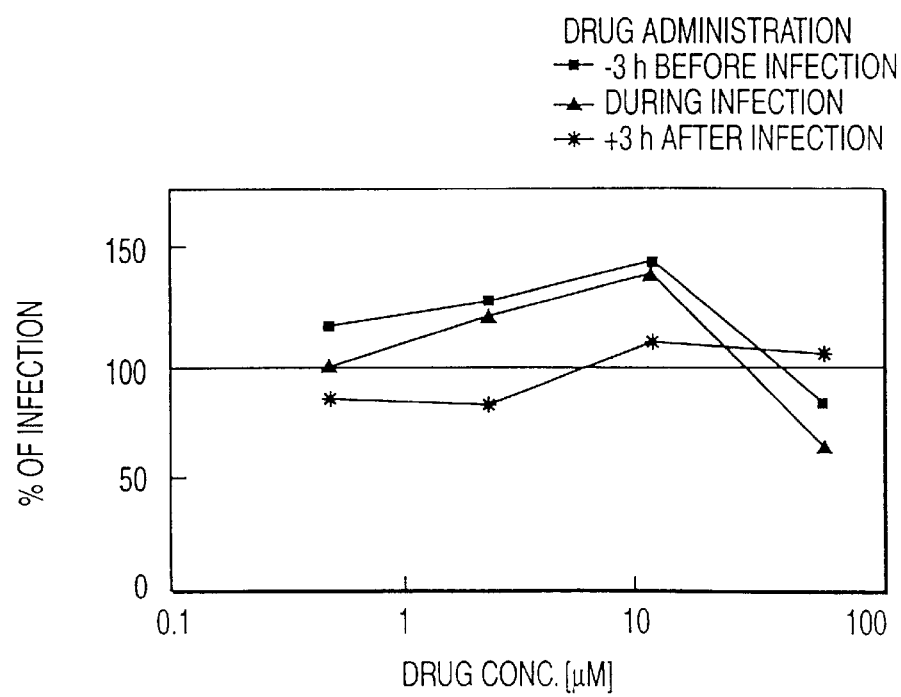
FIG. 2 shows the result of a single cycle experiment demonstrating the antiviral activity of Kon 2b (SEQ ID NO:31) aganist HSV-1 (Multiplicity of infection=10).

The invention will be further clarified by the following examples, which are intended to be purely exemplary of the invention.

All of the documents referred to in this application are herein incorporated by reference.

EXAMPLE 1

Preparation of a Support of the Formula IV a) Preparation of the support of the formula IVa by reacting aminopropyl-CPG with the succinate of bishydroxyethyl sulfone dimethoxytrityl ether 4.56 g of the dimethoxytrityl (DMTr) monoether of bis-(2-hydroxyethyl)sulfone (10 mmol) are dried by twice being taken up and concentrated in absolute (abs.) pyridine, and are dissolved in 25 ml of abs. pyridine, then 1.78 g (14 mmol) of DMAP (dimethylaminopyridine) and 1.4 g of succinic anhydride (14 mmol) are added and this mixture is stirred at room temperature for 3 hours. After the reaction is complete, the mixture is concentrated, the residue is taken up and concentrated three times in toluene to remove the pyridine, and then taken up in 220 ml of methylene chloride. The organic phase is washed with 10% strength citric acid (110 ml) and 3 times with 110 ml of water, dried over sodium sulfate and concentrated. The resulting solid residue is dried in vacuo (5.64 g).

1.67 g (3 mmol) of this succinate are taken up and concentrated twice in abs. pyridine and dissolved in a mixture of 0.65 ml of abs. pyridine and 6 ml of tetrahydrofuran (THF). A solution of 420 mg (3 mmol) of p-nitrophenol and 687 mg of DCC (dicyclohexylcarbodiimide, 3.3 mmol) in 2.1 ml of abs. THF is then added and the mixture is stirred at room temperature for two hours. Once the reaction is complete, the precipitated dicyclohexylurea is removed by centrifugation. The sediment is suspended in 1 ml of abs. ether and centrifuged once again. 1.5 g of the aminopropyl-CPG support from Fluka (500 Å, 100 µmol/g of amino group) are suspended in a mixture of 1.8 ml of abs. DMF and 350 µl of triethylamine, and the combined solutions of the nitrophenyl succinate ester, which have been decanted from the sediment, are added, and the mixture shaken at room temperature for 16 hours. The solid support is separated off and shaken at room temperature for one hour with 3 ml of capping reagent (acetic anhydride/2,6-lutidine/DMAP; each 0.25 M in THF) to block reactive groups. The derivatized CPG support is then filtered off with suction, washed with methanol, THF, methylene chloride, and ether and subsequently dried in vacuo at 40° C. The loading of the support of the formula IVa with dimethoxytrityl-containing component is 38 µmol/g.

b) Preparation of the support of the formula IVb by reacting TentaGel® (®=registered trademark of the Rapp company, Tübingen) with the succinate of the bishydroxy ethyl sulfone dimethoxytrityl ether.

100 mg of the amino form of the TentaGel resin, a PS/POE copolymer with 250 µmol/g amino group, are suspended in a mixture of 360 l of DMF and 70 µml of triethylamine, and 400 µmol of the p-nitrophenyl succinate ester (preparation see Ex. 1a) are added and the mixture is shaken at room temperature for 16 hours. The subsequent workup is as described in Ex. 1a). The loading of the TentaGel resin of the formula IVb with dimethoxytrityl-containing component is 98 µmol/g.

c) Preparation of the support IVc by reacting TentaGel (hydroxy form) with the phosphitylating reagent of the formula IX (Z"-DMTr-O—$CH_2CH_2$—S—$CH_2CH_2$—O—; $R^9$=N(i-$C_3H_7$)$_2$; $R^{10}$=O—$CH_2CH_2CN$)

50 mg of the hydroxy form of the TentaGel resin with 500 µmol/g hydroxyl group are reacted in acetonitrile at 22° C. with 10 equivalents of the phosphitylating reagent of the formula IX (Z"=DMTr-O—$CH_2CH_2$—S—$CH_2CH_2$—O—; $R^9$=N(i-$C_3H_7$,)$_2$; $R^{10}$=O—$CH_2CH_2CN$) in the presence of 25 equivalents of tetrazole. After oxidizing with iodine water (1.3 g of iodine in THF/water/pyridine; 70:20:5= v:v:v), working up is carried out as described in Example 1a. The loading of the support of the formula IVc with dimethoxytrityl-containing component is 247 µmol/g.

EXAMPLE 2

Preparation of Protected Nucleoside 3'-Phosphoramidites of the Formula VIII a) Preparation of VIIIa (B'=Cyt$^{iBu}$, Z=O—$CH_2CH_3$, $R^5$=$R^6$= i-$C_3H_7$)

2 mmol of the nucleoside 3'-phosphorobisamidite of the formula VI (B'-Cyt$^{iBu}$, $R^5$=$R^6$=$R^7$=$R^8$=i-$C_3H_7$) are taken up and concentrated twice in 20 ml of abs. acetonitrile and then dissolved in 20 ml of abs. acetonitrile. A solution of 2.4 mmol of ethanol and 1.2 mmol of sublimed tetrazole in 5 ml of abs. acetonitrile is then added dropwise over a period of 15 minutes. After stirring has been continued for a further 2.5 hours, the mixture is diluted with 75 ml of methylene chloride, and the organic phase is extracted with 50 ml of 5% strength sodium bicarbonate solution. The aqueous solution is washed twice with 50 ml of methylene chloride, the combined organic phases are dried over sodium sulfate and concentrated in vacuo. The residue is purified by column chromatography on silica gel with methylene chloride/n-heptane/triethylamine (45:45:10;v:v:v). 0.7 g of the required diastereomeric substance is obtained as a compound which is pure by thin-layer chromatography. ($^{31}$P-NMR σ=146.7, 147.5 ppm). Traces of the corresponding bis-ethyl phosphite are isolated as byproduct ($^{31}$P-NMR σ=139.3 ppm).

b) Preparation of VIIIb (B'=Thy, Z=O-i-$C_3H_7$, $R^5$=$R^6$=i-$C_3H_7$)

The preparation takes place by phosphitylation of the 5'-O-dimethoxytritylthymidine of the formula X (B'=Thy (β-position); R=DMTr, V=O, a-O, Y"=O; 2mmol) with the bisamidite of the formula IX (Z"=O-i-$C_3H_7$, $R^9$=$R^{10}$=N(i-$C_3H_7$)$_2$; 4 mmol) in the presence of tetrazole (0.5 mmol) in 10 ml of abs. methylene chloride. The mixture is worked up as in Example 2a ($^{31}$P-NMR σ=145.04 ppm, 145.66 ppm).

c) Preparation of VIIIc (B'=Cyty$^{iBu}$, Z=O-n-$C_6H_{13}$, $R^5$=$R^6$= i-$C_3H_7$)

In an analogous manner to Example 2a from the bisamidite of the formula VIa (B'=Cyt$^{iBu}$, $R^5$=$R^6$=$R^7$=$R^8$=i-$C_3H_7$) by reaction with one equivalent of n-hexanol with tetrazole catalysis ($^{31}$P-NMR 148.1 ppm, 148.5 ppm).

d) Preparation of VIII d (B'=Cyt$^{iBu}$, Z=O-n-C$_{18}$H$_{37}$, R$^5$=R$^6$=i-C$_3$H$_7$)

In an analogous manner to Example 2a from the bisamidite of the formula VIa (B'=Cyt$^{iBu}$, R$^5$=R$^6$=R$^7$=R$^8$=i-C$_3$H$_7$) by reaction with one equivalent of n-octadecanol with tetrazole catalysis ($^{31}$P-NMR 147.2 ppm, 147.9 ppm).

e) Preparation of VIIIe (B'=Cyt$^{Bz}$, Z=3-pyridylpropan-3-oxy, R$^5$=R$^6$=R$^7$=R$^8$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$, R$^2$,=H by reaction with one equivalent of 3-pyridine (propan-3-ol) with tetrazole catalysis. In this case, it was possible to separate the two diastereomers by column chromatography ($^{31}$P-NMR diastereomer 1: 147.7 ppm, diastereomer 2: 148.2 ppm)

f) Preparation of VIIIf (B'=Cyt$^{Bz}$, Z=p-nitrophenylethyl-2-oxy, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with one equivalent of p-nitrophenylethan-2-ol with tetrazole catalysis ($^{31}$P-NMR 148.1 ppm, 148.6 ppm).

g) Preparation of VIIIg (B'=Cyt$^{Bz}$, Z=—(OCH$_2$CH$_2$)$_3$, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with equivalent of triethylene glycol monomethyl ether with tetrazole catalysis ($^{31}$P-NMR 148.5 ppm, 148.9 ppm).

h) Preparation of VIIIh (B'=Cyt$^{Bz}$, Z=—(OCH$_2$CH$_2$)$_4$O(CH$_2$)$_9$CH$_3$, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with one equivalent of tetraethylene glycol monodecyl ether with tetrazole catalysis ($^{31}$P-NMR 148.4 ppm, 148.8 ppm).

i) Preparation of VIIIi (B'=Cyt$^{Bz}$, Z=—(OCH$_2$CH$_2$)$_5$O(CH$_2$)$_4$CH$_3$, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with one equivalent of pentaethylene glycol monopentyl ether with tetrazole catalysis ($^{31}$P-NMR 148.4 ppm, 148.9 ppm).

k) Preparation of VIIIk (B'=Cyt$^{Bz}$, Z=—(OCH$_2$CH$_2$)$_8$O(CH$_2$)$_{13}$CH$_3$, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with one equivalent of octaethylene glycol monotetradecyl ether with tetrazole catalysis ($^{31}$P-NMR 148.4 ppm, 148.8 ppm).

l) Preparation of VIIIp (B'=Thy, Z=CH$_3$, R$^5$=R$^6$=i-C$_3$H$_7$)

In an analogous manner to Example 2b from 5'-O-dimethoxytritylthymidine by phosphitylation with the reagent of the formula IX (Z"=CH$_3$, R$^9$=Cl, R$^{10}$=N(i-C$_3$H$_7$)$_2$, where, instead of tetrazole, catalysis is effected with two equivalents of diisopropylethylamine ($^{31}$P-NMR 120.6 ppm, 121.0 ppm).

m) Preparation of VIIIm (B'=Cyt$^{Bz}$, Z=acridine-9-(butyl-4-oxy)-, R$^5$=R$^6$=i-C$_3$H$_7$)

In an analogous manner to Example 2a from the bisamidite of the formula VIa (B'=Cyt$^{Bz}$, R$^5$=R$^6$=R$^7$=R$^8$=i-C$_3$H$_7$) by reaction with one equivalent of 9-(4-hydroxybutyl)-acridine with tetrazole catalysis ($^{31}$P-NMR 146.7 ppm, 147.4 ppm).

EXAMPLE 3

Preparation of the Support-Bound Nucleotide of the Formula VII a) Method A: Preparation of a support of the formula VIIa-1 by coupling the nucleoside 3'-phosphoramidite of the formula VIIIb 7.5 mg of the support from Example 1a, to which is bound 0.2 μmol of the bishydroxyethyl sulfone dimethoxytrityl ether, are treated with 3% strength trichloroacetic acid, thereby removing the DMTr protective group, washed with acetonitrile, and subsequently reacted with 2 μmol of the nucleoside 3'-phosphoramidite of the formula VIIIb (B'=Thy, Z=O-i-C$_3$H$_7$, R$^5$=R$^6$=i-C$_3$H$^7$) in the presence of tetrazole (10 μmol) in acetonitrile. The reaction time is 2.5 minutes. Oxidation with iodine (for W=O; 1.3 g of iodine in THF/water/pyridine; 70:20:5=v:v:v) then takes place.

b) Method B: Preparation of a support of the formula VIIa-2 by reaction via the phosphitylation reagent of the formula IX The phosphitylation reagent of the formula IX (Z"=n-octyl, R$^9$=R$^{10}$=Cl; 1 equivalent) is reacted in the presence of 1.2 equivalents of diisopropylethylamine (DIPEA) in abs. acetonitrile or methylene chloride with a nucleoside of the formula X (1 equivalent of 5'-O-dimethoxytrityl-thymidine, B'=β-position, Y'''=O,) at −78° C. to form the corresponding nucleoside-3'-O-n-octylphosphone monochloride. To remove the protective group D=DMTr, the support of the formula IVa is treated as described in Method A, and then washed with acetonitrile and reacted with an excess of the nucleoside-3'-O-n-octylphosphone monochloride, prepared in situ, in the presence of DIPEA. After oxidation with iodine water, a support-bound nucleotide of the formula VIIa-2 is obtained, which is available for the subsequent oligonucleotide synthesis.

EXAMPLE 4

Preparation of Oligonucleotides of the Formula I (the Monomer is in Each Case a β-D-deoxyribonucleoside)

a) Preparation of an oligonucleotide of the formula Ia (R$^1$=R$^2$=H, Z=O-i-C$_3$H$_7$, a=U=V=W=X=Y=Y'=0, B=Thy, n=9)

TpTpTpTpTpTpTpTpTp-(O-i-C$_3$H$_7$)

0.2 μmol of the support VIIa-1 (B'=Thy, W=O, Z=O-i-C$_3$H$_7$) from Example 3a is treated with the following reagents in turn:

1. Abs. acetonitrile
2. 3% Trichloroacetic acid in dichloromethane
3. Abs. acetonitrile
4. 4 μmol of β-Cyanoethyl 5'-O-dimethoxytrityl-thymidine-3'-phosphite-diisopropylamidite and 25 μmol of tetrazole in 0.15 ml of abs. acetonitrile.
5. Acetonitrile
6. 20% Acetic anhydride in THF with 40% lutidine and 10% dimethylaminopyridine
7. Acetonitrile
8. Iodine (1.3 g in THF/water/pyridine; 70:20:5=v:v:v)

The steps 1 to 8, hereinafter termed one reaction cycle, are repeated 8 times to construct the decathymidylate derivative. After the synthesis has been completed, removal of the dimethoxytrityl group takes place as described in steps 1 to 3. The oligonucleotide is cleaved from the support, and the β-cyanoethyl groups are simultaneously eliminated, by treatment for 1.5 hours with ammonia. Since the oligonucleotide does not contain any amino-protective groups, no further treatment with ammonia is necessary. The resultant crude product of isopropyl decathymidylate 3'-phosphate is purified by polyacrylamide gel electrophoresis or HPLC.

b) Preparation of an oligonucleotide of the formula Ib ($R^1=R^2=H$, $Z=O$-i-$C_3H_7$, $a=U=V=W=X=Y=Y'$-O)

d(CpGpTpCpCpApTpGpTpCpGpGpCpApApApCpApGpCpTp-O-i-$C_3H_7$)

The synthesis takes place in an analogous manner to Example 4a, but with different nucleotide bases in the monomer. In synthesis steps 1 to 8, the monomer is generally employed as a β-cyanoethyl 5'-O-dimethoxy-trityl-nucleoside-3'-phosphite-dialkylamide, where the amino group of adenine (Ade), cytosine (Cyt), or guanine (Gua) is provided with suitable protective groups. In this example, $N^6$-benzoyl-Ade ($Ade^{Bz}$), $N^4$-benzoyl-Cyt ($Cyt^{Bz}$), and $N^2$-isobutyryl-Gua ($Gua^{iBu}$) are used. Chain construction takes place as described in Example 4a, starting with the support of the formula VIIa-1 (B'=Thy, W=O, Z=O-i-$C_3H_7$), and condensing on the corresponding monomers according to the above sequence. However, to remove the amino-protective groups, an additional treatment with ammonia (50° C. for 16 hours) is carried out.

c) Preparation of an oligonucleotide of the formula Ic ($R^1=R^2=H$, $Z=O$—$CH_2CH_3$, $a$=-$U=V=W=Y=Y'$=O)

d(CpGpTpCpCpApTpGpTpCpGpGpCpApApApCpApGpCp-O—$CH_2CH_3$)

Starting with the support of the formula VIIa-3 (B'= $Cyt^{iBu}$, W=O, Z=O—$C_2H_5$), whose preparation takes place with the aid of the monomer of the formula VIIIa according to method A (Example 3a), the synthesis is carried out in an analogous manner to Example 4b. However, the more labile amino-protective groups $N^6$-phenoxyacetyl-Ade ($Ade^{PAC}$), $N^4$-isobutyryl-Cyt ($Cyt^{iBu}$) and $N^2$-phenoxyacetyl-Gua ($Gua^{PAC}$), which are easier to cleave at the end of the synthesis, are advantageously used to prepare base-labile substitutions (as here for Z=O—$C_2H_5$). Removal of the protective groups with ammonia then only takes 2 hours at 50° C. If the product is treated with ammonia for a further 6 hours at 50° C., about 5 to 10 percent of the oligonucleotide-3'-phosphate is obtained as a byproduct as a result of cleavage of the ethyl phosphate ester.

d) Preparation of an oligonucleotide of the formula Id ($R^1=R^2=H$, $Z=O$—$(CH_2)_{17}CH_3$, $a=U=V=X=Y=Y'$=O; W=O, except for the last two 5'-terminal phosphorothioate internucleotide bonds, where W=S (indicated as $p_s$))

d($Cp_sGp_s$TpCpCpApTpGpTpCpGpGpCpApApApCpApGpCp-O—$(CH_2)_{17}CH_3$)

Starting with the support of the formula VIIa-4 (B'= $Cyt^{iBu}$, W=O, Z=O—$(CH_2)_{17}CH_3$), whose preparation takes place with the aid of the monomer of the formula VIIId according to method A (Example 3a), the synthesis is carried out with the more labile protective groups in an analogous manner to that described in Example 4c. After coupling the penultimate nucleotide (G) and the last nucleotide (C), a TETD solution (0.4 M tetraethylthiuram disulfide in acetonitrile) is employed for the sulfur oxidation instead of iodine water. The protective groups are removed by treatment with ammonia for 2 hours. An oligonucleotide of the formula Id is obtained with two 5'-terminal phosphorothioate internucleotide bonds and a 3'-O-n-octadecyl phosphate ester residue.

e) Preparation of an oligonucleotide of the formula Ie ($R^1=R^2=H$, $Z=CH_3$, $a=V=W=X=Y=Y'$=O; U=O, except for the two 5'-terminal methylphosphonate internucleotide bonds, where U=$CH_3$ (indicated as $p_{Me}$))

d($Cp_{Me}Gp_{Me}$TpCpCpApTpGpTpCpGpG-pCpApApApCpApGpCpTp$_{Me}$)

Starting with the support of the formula VIIa-5 (B'=Thy, W=O, Z=$CH_3$), whose preparation takes place with the aid of the monomer of the formula VIIIp according to method A (Example 3a), the synthesis is carried out in an analogous manner to Example 4c. Instead of the normal cyanoethyl-protected monomers (formula VIII, Z=$OCH_2CH_2CN$), the corresponding methylphosphonamidites (formula VIII, Z=$CH_3$) are employed for coupling the last two nucleotide units (G and C). Cleavage from the support with concentrated (conc.) ammonia (1.5 hours at room temperature) is followed by a 6-hour treatment with ethylenediamine/ethanol/water (5:4:1; v:v:v) to liberate the amino groups of the bases. The result is an oligonucleotide-3'-methylphosphonate with two 5'-terminal methylphosphonate internucleotide bonds of the formula Ie.

f) Preparation of an oligonucleotide of the formula If ($R^1=R^2=H$, $Z=CH_3$, X=S, $a=U=V=W=Y=Y'$=O)

d(CpGpTpCpCpApTpGpTpCpGpGpCpApApApCpApGpCp$_{(S)Me}$)

Starting with the support of the formula IVa from Example 1a, the methylphosphonamidite of the formula VIII (Z=$CH_3$, B'=$Cyt^{iBu}$, $R_5=R_6$=i-$C_3H_7$) is coupled in the first reaction cycle as described in Example 3a. Oxidation is carried out with TETD. Further synthesis is as described in Example 3c. After removal of the protective groups in an analogous manner to Example 3e, an oligonucleotide-3'-methylphosphonothioate of the formula If is obtained.

g) Preparation of an oligonucleotide of the formula Ig ($R^1=R^2=H$, Z=X=S, $a=U=V=W=Y=Y'$=O)

d((CpGpTpCpCpApTpGpTpCpGpGpCpApApApCpApGpCp$_{(S)}$S)

In analogy with the synthesis described in Example 4b, starting with the support of the formula IVa from Example 1a, with the difference, however, that in the first condensation step, a nucleoside-3'-phosphoramidite of the formula VIII (Z=2,4-dichlorothiobenzyl; $R^5$–$R^6$=ethyl) is employed instead of the methylphosphonamidite. Once again, the introduction of the second S atom takes place by oxidation with TETD (0.4 M in acetonitrile). Cleavage of the dichlorobenzylthio group takes place in a known manner with thiophenol/triethylamine. After removal of the protective groups with conc. ammonia, an oligonucleotide-3'-phosphorodithioate of the formula Ig is obtained.

h) Preparation of an oligonucleotide of the formula Ih ($R^1=R^2=H$, Z=p-nitrophenylethyl-2-oxy, $a=U=V=W=X=Y=Y'$=O)

d (CpGpTpCpCpApTpGpTpCpGpGpCpApApApCpApGpCp—O—CH$_2$CH$_2$——NO$_2$)

Starting with the support of the formula VIIa-6 (B'=Cyt$^{Bz}$, W=O, Z=p-nitrophenylethyl-2-oxy), whose preparation takes place with the aid of the monomer of the formula VIIIf according to method A (Example 3a), the synthesis is carried out in an analogous manner to Example 4b. After removal of the protective groups by 10-hour treatment with ammonia at 55° C., an oligonucleotide-3'-O-(p-nitrophenylethyl) phosphate of the formula Ih is obtained.

i) Preparation of an oligonucleotide of the formula Ii (R$^1$=R$^2$=H, Z=3-pyridylpropan-3-oxy, a=U=V=W=X=Y=Y'=O)

d (CpGpTpCpCpApTpGpTpCpGpGpCpApApApCpApGpCp—O—(CH$_2$)$_3$—)

Starting with the support of the formula VIIa-7 (B'=Cyt$^{iBu}$, W=O,

Z = —O—(CH$_2$)$_3$—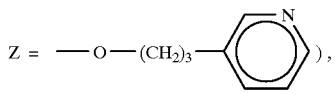), which was prepared with the aid of the amidite of the formula VIIIe as described in Example 3a, the oligonucleotide synthesis takes place in analogy with Example 4c.

k) Preparation of an oligonucleotide of the formula Ik (R$^1$=R$^2$=H, Z=—O—(CH$_2$CH$_2$O)$_3$CH$_3$, a=U-V-W=X=Y=O)

d(GpApGpGpApCpGpTpTpCpCpT-pCpCpTpGpCpGpGpGpApApGpGpCp-O—(CH$_2$CH$_2$O)$_3$CH$_3$)

Starting with the support of formula VIIa-8 (B'=Cyt$^{Bz}$, W=O, Z=—O—(CH$_2$CH$_2$O)$_3$CH$_3$, which was prepared with the aid of the amidite of the formula VIIIg as described in Example 3a, the oligonucleotide synthesis corresponding to the above sequence takes place in analogy with Example 4b.

l) Preparation of an oligonucleotide of the formula Il (R$^1$=R$^2$=H, Z=—O—(CH$_2$CH$_2$O)$_5$(CH$_2$)$_4$CH$_3$, a=U=V=W=X=Y=Y'=O)

d(CpGpTpCpCpApTpGpTpCpGpGpGpCpApApApCpApGpCp-O—(CH$_2$CH$_2$O)$_5$—(CH$_2$)$_4$CH$_3$)

Starting with the support of the formula VIIa-9 (B'=Cyt$^{Bz}$, W=O, Z=—O—(CH$_2$CH$_2$O)$_5$(CH$_2$)$_4$CH, which was prepared with the aid of the amidite of the formula VIIIi as described in Example 3a, the oligonucleotide synthesis takes place in analogy with Example 4b.

m) Preparation of an oligonucleotide of the formula Im (R$^1$=R$^2$=H, Z=—O—(CH$_2$CH$_2$O)$_8$(CH$_2$)$_{13}$CH$_3$, a=U=V=W=X=Y=Y'=O)

d(CpGpTpCpCpApTpGpTpCpGpGpGpCpApApApCpApGpCp-O—(CH$_2$CH$_2$O)$_8$—(CH$_2$)$_{13}$CH$_3$)

Starting with the support of the formula VIIa-10 (B'=Cyt$^{Bz}$, W=O, Z=—O—(CH$_2$CH$_2$O)$_8$(CH$_2$)$_{13}$CH$_3$), which was prepared with the aid of the amidite of the formula VIIIk as described in Example 3a, the oligonucleotide synthesis takes place in analogy with Example 4b.

n) Preparation of an oligonucleotide of the formula In (R$^1$=R$^2$=H, Z=—(CH$_3$)N(CH$_2$)$_2$N(CH$_3$)$_2$, a=U=V=W=X=Y=Y'=O)

d(CpGpTpCpCpApTpGpTpCpGpGpGpCpApApApCpApGpCp-N(CH$_3$)(CH$_2$)$_2$N—(CH$_3$)$_2$

Starting with the support of the formula IVc from Example 1c, the oligonucleotide synthesis is carried out as described in Example 4a, with the exception that a methoxyphosphoramidite of the formula VIII (B'=Cyt$^{i-Bu}$, Z=OCH$_3$, R$^5$=R$^6$=N(i-C$_3$H$_7$)$_2$ is employed for the first condensation reaction and the oxidative amidation takes place for two times 15 minutes with a 0.1 M iodine solution in THF/N;N',-trimethylethylenediamine (2:1;v:v). After construction of the oligonucleotide sequence, the base-stable sulfide support is oxidized with NaIO$_4$ in a manner known per se to the base-labile sulfone support. Cleavage from the support and removal of the protective groups (PAC for Ade and Gua; i-Bu for Cyt) is effected with t-butylamine/methanol (1:1;v:v) at 50° C. for 16 hours. An oligonucleotide-3'-trimethylethylenediamine-phosphramidate of the formula In is obtained.

o) Preparation of an oligonucleotide of the formula Io (R$^1$=R$^2$=H, Z=HN(CH$_2$)$_2$O—CH$_3$, a=U=V=W=X=Y=Y'=O)

d(CpGpTpCpCpApTpGpTpCpGpGpGpCpApApApCpApGpCp-HN(CH$_2$)$_2$O—CH$_3$)

In analogy with Example 4n, the oxidative amidation with 0.1 M iodine solution in THF/2-methoxy-ethylamine (2:1;v:v) takes place for two times 15 minutes. After removal of the protective groups, an oligonucleotide-3'-(2-methoxyethyl)-phosphoramidate of the formula Io is obtained.

p) Preparation of an oligonucleotide of the formula Ip (R$^1$=formula II, R$^2$=H, Z=S, a=U=V=W=X=Y=Y'=Z'=O)

d(p$_s$CpGpTpCpCpApTpGpTpCpGpGpGpCpApApApCpApGpCp$_s$)

The synthesis is carried out as described in Example 4b, starting with the support of the formula IVa. However, after coupling the first unit (formula VIII; B'=Cyt$^{Bz}$; Z=O—CH$_2$CH$_2$CN; R$^5$=R$^6$=N(i-C$_3$H$_7$)$_2$) oxidation is carried out with TETD. After removal of the DMTr protective group of the last base added, the free 5'-hydroxyl group is phosphitylated with the bis-cyanoethyloxy-phosphoramidite of the formula IX (R$^9$=N(i-C$_3$H$_7$)$_2$, Z"=R$^{10}$=OCH$_2$CH$_2$CN, and subsequently oxidized to the thiophosphate with TETD. The cyanoethyl-protective groups are eliminated during ammonia treatment. The result is an oligonucleotide-3',5'-bis-thiophosphate of the formula Ip.

q) Preparation of an oligonucleotide of the formula Iq ($R^1$=formula II, $R^2$=H, Z=O-i-$C_3H_7$, a=U=V=W=X=Y=Y'=Z'=O)

The synthesis is carried out as described in Example 4b. After removal of the DMTr protective group of the last base added, the free 5'-hydroxyl group is phosphitylated with the cyanoethyloxy-i-propyloxy-phosphoramidite of the formula IX ($R^9$=N(i-$C_3H_7$)$_2$, $R^{10}$=OCH$_2$CH$_2$CN, Z"=O-i-$C_3H_7$, and subsequently oxidized with iodine water. The result is an oligonucleotide-3'5'-bis-isopropyl phosphate ester of the formula Iq.

r) Preparation of an oligonucleotide of the formula Ir ($R^1$= formula II, $R^2$=H, Z=n-$C_8H_{17}$, a=U=V=W=X=Y=Y'=Z'=O)

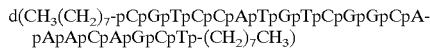

Starting with the support of the formula VIIa-2 (B'=Thy, W=O, Z=(CH$_2$)$_7$CH$_3$), whose preparation is described in Example 3b, the synthesis is carried out in analogy with Example 4c. After removal of the DMTr protective group of the last base added, the free 5'- hydroxyl group is phosphitylated with n-octyldichlorophosphane of the formula IX (Z"=(CH$_2$)$_7$CH$_3$, $R^9$–$R^{10}$=Cl) using DIPEA (diisopropylethylamine). After oxidation and hydrolysis, the oligonucleotide is cleaved from the support as in Example 4e. An oligonucleotide-3'5'-bis-(n-octylphosphonate) of the formula Ir is obtained.

s) Preparation of an oligonucleotide of the formula Is ($R^1$=$R^2$=H, Z="psoralen", a=U=V=W=X=Y=Y'=O

The synthesis takes place in analogy with Example 4c starting with the support of the formula VIIa-11 (B'=Gua$^{PAC}$, Z="psoralen", W=O), which was prepared in analogy with Example 3a from the monomer of the formula VIII (B'= Gua$^{PAC}$, Z="psoralen", $R^5$=$R^6$=i-$C_3H_7$), which had previously been obtained from the bisamidite VIa (B'=Gua$^{PAC}$, $R^5$–$R^8$=i-$C_3H_7$) by reaction with "psoralen"-H (U. Pieles and U. Englisch, Nucleic Acids Research 17:285 (1989)) in analogy with Example 2a. After removal of the protective groups with ammonia, an oligonucleotide of the formula I is obtained, to which a "psoralen' phosphate ester is bound at the 3'-end.

t) Preparation of an oligonucleotide of the formula ($R^1$=$R^2$= H, Z="biotin", a=U=V=W=X=Y=Y'=O)

The synthesis takes place in analogy with Example 4c starting with the support of the formula VIIa-12 (B'=Gua$^{PAC}$, z="biotin", W=O), which was prepared in analogy with Example 3a from the monomer of the formula VIII (B'= Gua$^{PAC}$, z="biotin", $R^5$=$R^6$=i-$C_3H_7$), which had previously been obtained from the bisamidite VIa (B'=Gua$^{PAC}$, $R^5$–$R^8$= i-$C_3H_7$) by reaction with "biotin"-H (R. Pon, Tetrahedron Lett. (1991) 32, 1715) in analogy with Example 2a. After removal of the protective groups with ammonia, an oligonucleotide of the formula it is obtained, to which a "biotin" phosphate ester is bound at the 3'-end.

u) Preparation of an oligonucleotide of the formula Iu ($R^1$=$R^2$=H, Z="fluorescein", a=U=V=W=X=Y=Y'=O)

The synthesis takes place in analogy with Example 4c, starting with the support of the formula VIIa-13 (B'=Gua$^{PAC}$, z="fluorescein", W=O), which was prepared in analogy with Example 3a from the monomer of the formula VIII (B'= Gua$^{PAC}$, Z="fluorescein", $R^5$=$R^6$=i-$C_3H_7$), which had previously been obtained from the bisamidite VIa (B'=Gua$^{PAC}$, $R^5$–$R^8$=i-$C_3H_7$) by reaction with "fluorescein"-H (Schubert et al., Nucleic Acids Research (1991) 18,3427) in analogy with Example 2a. After removal of the protective groups with ammonia, an oligonucleotide of the formula Iu is obtained, to which a "fluorescein" phosphate ester is bound at the 3'-end.

v) Preparation of an oligonucleotide of the formula Iv ($R^1$=$R^2$=H, Z=acridin-9-yl-but-4-oxy, a=U=V=W=X=Y=Y'=O)

Starting with the support of the formula VIIa-14 (B'= Cyt$^{BZ}$, W=O, Z=acridin-9-yl-but-4-oxy), whose preparation takes place using the monomer of the formula VIIIm in analogy with Example 3a, the oligonucleotide synthesis is carried out as described in Example 4b. After deprotection, an oligonucleotide of the formula Iv is obtained, which contains an acridin-9-yl-but-4-yl phosphate ester at the 3'-end.

w) Preparation of an oligonucleotide of the formula Iw ($R^1$=$R^2$=H, Z=HN(CH$_2$)$_3$NH(CH$_2$)$_4$NH(CH$_2$)$_3$NH$_2$, a=U=V=W=X=Y=Y'=O)

The synthesis takes place in analogy with Example 4n, with the oxidative amidation being carried out with spermine. A capping reaction is then carried out with trifluoroacetic anhydride instead of acetic anhydride. After removing the protective groups, an oligonucleotide of the formula Iw is obtained, which contains a sperminephosphoramidate residue at the 3'-end.

x) Preparation of an oligonucleotide of the formula Ix ($R^1$=$R^2$=H, Z=aziridyl-N-ethyl-2-oxy, a=U=V=W=X=Y=Y'=O)

The synthesis takes -place in analogy with Example 4c, starting with the support of the formula VIIa-15 (B'=Cyt$^{Bz}$, Z=aziridyl-N-ethyl-2-oxy, W=O), which was prepared in analogy with Example 3a from the monomer of the formula VIII (B'=Cyt$^{Bz}$, Z=aziridyl-N-ethyl-2-oxy, $R^5$=$R^6$=i-$C_3H_7$), which had previously been obtained from the bisamidite of the formula VIa (B'=Cyt$^{Bz}$, R$^5$–R$^8$=iC$_3$H$_7$) by reaction with N-(2-hydroxyethyl)aziridine in analogy with Example 2a. After removal of the protective groups with ammonia, an oligonucleotide of the formula Ix is obtained, to which an aziridine-N-eth-2-yl phosphate ester is bound at the 3'-end.

y-1) Preparation of an oligonucleotide of the formula Iy-1 (R$^1$=R2=H, Z=—O-farnesyl, for ps is W=S)

Z=O-"cholesterol"), which, in analogy with Example 3a, was prepared from the monomer of the formula VIII (B'=Thy, Z=O-"cholesterol", R$^5$=R$^6$=i-C$_3$H$_7$), which had previously been obtained from the bisamidite VIa (B'=Thy, R$^5$–R$^8$=i-C$_3$H$_7$) by reaction with "cholesterol" in analogy with Example 2b. The nucleotides 2, 3, 19, and 20 are 5'  CpSCpSGpSGpSApSApSApSApSCpSApSTpSCpSGpSCpSGpSGpSTpSTpSGpSTpS—O—farnesyl The synthesis takes place in analogy with Example 4d, starting with the support of the formula VIIa-16 (B'=Thy, Z=O-farnesyl), which, in analogy with Example 3a, was prepared from the monomer of the formula VIII (B'=Thy, Z=O-farnesyl, R$^5$=R$^6$=i-C$_3$H$_7$), which had previously been prepared from the bisamidite VIa (B'=Thy, R$^5$–R$^8$=i-C$_3$H$_7$) by reaction with farnesol in analogy with Example 2b. In this case, the oxidation is carried out on each occasion with TETD solution as described in Example 4d. After removal of the protective groups with ammonia, an allophosphorothioate oligonucleotide of the formula Iy-1 is obtained, to which a farnesyl thiophosphate ester is bound at the 3'-end.

y-2) Preparation of an oligonucleotide of the formula Iy-2 (R$^1$=R$^2$=H, Z=—O-phytyl for ps(s) is W=U=S)

introduced, as described in Example 4e, via the methylphosphonamidites of the formula VIII (Z=CH$_3$). In each case oxidation is with iodine water. After removal of the protective groups (cf. Example 4d), an oligonucleotide of the formula Iy-3 is obtained, which in each case has two methylphosphonate internucleoside bonds 3'- and 5'-terminally, and to which a "cholesterol" phosphate ester is bound at the 3'-end.

y-4) Preparation of an oligonucleotide of the formula Iy-4 (R$^1$=R$^2$=H, Z=—O-testosterone, for pMe is U=CH$_3$)

5'  CpMeCpMeGpMeGpMeApMeApMeApCpApTpCpGpCpMeGpMeGpMe—TpMeTpMeGpMeTp—"testosterone"

5'  Cp(S)CpS(S)GpGpApApApCpApTpCpGpCpGGpTpTpS(S)GpS(S) Tp—O—phytyl3'

The synthesis takes place in analogy with Example 4y-1, starting with the support of the formula VIIa-17 (B'=Thy, Z=O-phytyl), which, in analogy with Example 3a, was prepared from the monomer of the formula VIII (B'=Thy, z=O-phytyl, R$^5$=R$^6$=i-C$_3$H$_7$), which had previously been obtained from the bisamidite VIa (B'=Thy, R$^5$–R$^8$-i-C$_3$H$_7$) by reaction with phytol in analogy with Example 2b. The nucleotides 2, 3, 19, and 20 (counting of the nucleotides corresponds to the direction of synthesis from 3' to 5') are [?] via the units of the formula VIII (Z=2,4-dichlorothiobenzyl, R$^5$, R$^6$=C$_2$H$_5$). In the case of these nucleotides, oxidation is carried out with TETD solution. In the other reaction cycles, oxidation is with iodine water. After removal of the protective groups with ammonia, an oligonucleotide of the formula Iy-2 is obtained, which, in each case, has two phosphorodithioate internucleoside bonds 3'- and 5'-terminally, and to which is bound a farnesyl phosphate ester at the 3'-end.

The synthesis takes place in analogy with Example 4y-3, starting with the support of the formula VIIa-19 (B'=Thy, Z=O-"testosterone"), which, in analogy with Example 3a, was prepared from the monomer of the formula VIII (B'=Thy, Z=O-"testosterone", R$^5$=R$^6$=i-C$_3$H$_7$), which had previously been obtained from the bisamidite VIa (B'=Thy, R$^5$–R$^8$-i-C$_3$H$_7$) by reaction with "testosterone" in analogy with Example 2b. The nucleotides 2 to 7 and 15 to 20 are, as described in Example 4e, introduced via the methylphosphonamidites of the formula VIII (Z=CH$_3$). In each case oxidation is with iodine water. After removal of the protective groups, an oligonucleotide of the formula Ly-4 is obtained, which in each case has six methylphosphonate internucleoside bonds 3'- and 5'-terminally, and to which a "testosterone" phosphate ester is bound at the 3'-end.

y-5) Preparation of an oligonucleotide of the formula ly-5 (R$^1$=R$^2$=H, Z=—O-vitamin A for pMe(S) is U=CH$_3$ and W=S, for pS is U=S and W=O)

CpMe(S)CpMe(S)GpMe(S)GpMe(S)ApMe(S)ApMe(S)ApSApSCpSApSTpSCpGp

ṠCpMe(S)GpMe(S)GpMe(S)TpMe(S)TpMe(S)TpMe(S)GpMe(S)Tp—O-"Vitamin A"

y-3) Preparation of an oligonucleotide of the formula Iy-3 (R$^1$=R$^2$=H, Z="—O-cholesterol", for pMe is U=CH$_3$)

5'CpMeCpMeGpGpApApApApCpApT-
pCpGpCpGpGpTpTpMeGpMeTp-"O-cholesterol"

The synthesis takes place in analogy with Example 4y-1, starting with the support of the formula VIIa-18 (B'=Thy, The synthesis takes place in analogy with Example 4y-4 starting with the support of the formula VIIa-20 (B'=Thy, Z=O-"Vitamin A"), which, in analogy with Example 3a, was prepared from the monomer of the formula VIII (B'=Thy, Z=O-"Vitamin A", R$^5$=R$^6$=iC$_3$H$_7$), which had previously been obtained from the bisamidite VIa (B'=Thy, R$^5$R$^6$=iC$_3$H$_7$) by reaction with "Vitamin A-alcohol" in analogy with Example 2b. The nucleotides 2 to 7 and 15 to 20 are introduced via methylphosphoramidites of the formula VIII (Z=CH$_3$) as described in Example 4e. Oxidation is with TETD as described in Example 4d. After removing protective groups, an oligonucleotide of the formula ly-5 is obtained, which contains methylphosphonothioate and internally seven phosphorothioate internucleoside bonds. A "vitamin A" phosphate ester is additionally located at the 3'-end of this oligonucleotide.

Y-6) Preparation of an oligonucleotide of the formula ly-6 (R$^1$=H, R$^2$=O—CH$_3$; R$^2$=H for T, Z=—O-vitamin E)

2'-O—CH$_3$(CpCpGpGpApApApApCpApUpCpGpCpGpGpUpUpGp)T p-O-"vitamin E"

The synthesis takes place in analogy with Example 4y-4, starting with the support of the formula VIIa-21 (B'=Thy, Z=O-"vitamin E"), which, in analogy with example 3a, was prepared from the monomer of the formula VIII (B'=Thy, Z=O-"vitamin E", R$^5$=R$^6$=i-C$_3$H$_7$), which had previously been obtained from bisamidite VIa (B'=Thy, R$^5$–R$^8$=i-C$_3$H$_7$) by reaction with tocopherol in analogy with Example 2b. The nucleotides 2 to 20 are introduced via the 2'-O-methylribonucleoside-phosphoramidites of the formula V (R=DMTr, R$^2$=O—CH$_3$H$_7$). Oxidation is with iodine water, as described in Example 4a. After removing the labile phenoxyacetyl protective groups, a 2'-O-methyloligoribonucleotide of the formula ly-6 is obtained, which contains a "vitamin E" phosphate ester at the 3'-end.

EXAMPLE 5

Preparation of the Phosphitylating Reagent DMTr-O—CH$_2$CH$_2$—S—CH$_2$CH$_2$O—P—(OCH$_2$CH$_2$CN)(N(i-C$_3$H$_7$)$_2$)

The bis-hydroxyethyl sulfide (3.05 g) is dissolved in 75 ml of abs. pyridine and this solution is cooled to 0° C. The dimethoxytrityl chloride (8.04 g) dissolved in 60 ml of abs. pyridine is then added dropwise with stirring over a period one hour. After warming the reaction mixture at room temperature, this is stirred for a further 1.5 hours. 5 ml of water are added to the solution, which is then concentrated in vacuo. The residue is dissolved in 250 ml of methylene chloride. This solution is extracted three times with 125 ml of 0.1 M phosphate buffer, pH 7, on each occasion, and the organic phase is dried over sodium sulfate and concentrated in vacuo. The crude product is chromatographed on a silica gel column using ethyl acetate/n-heptane/triethylamine (gradient 6:14:1 to 2:2:1, v:v:v). 5.3 g of the bis-hydroxyethyl sulfide-mono-(dimethoxytrityl)ether DMTr-O—CH$_2$CH$_2$—S—CH$_2$CH$_2$OH (52%) are obtained.

A solution of this dimethoxytrityl compound (1.06 g) and of tetrazole (88 mg) in 12.5 ml of abs. acetonitrile is slowly (20 min) added dropwise to a solution of cyanoethoxy-diisopropylamino-phosphane (0.75 g) in abs. acetonitrile (20 ml). After a further 3 hours of reaction, the reaction solution is diluted with 95 ml of methylene chloride and washed with 5% strength sodium carbonate solution (65 ml). The organic phase is dried over sodium sulfate and concentrated in vacuo. The residue is purified by chromatography on a silica gel column with ethyl acetate/n-hexane/triethylamine (11:8:1, v:v:v). 1.25 g (80%) of the required phosphitylating reagent ($^{33}$P-NMR: σ 148 ppm [d], 99% of the total phosphorus content) are obtained.

The compounds y-1 to y-6 described in Example 4 possess residues of the following definition:

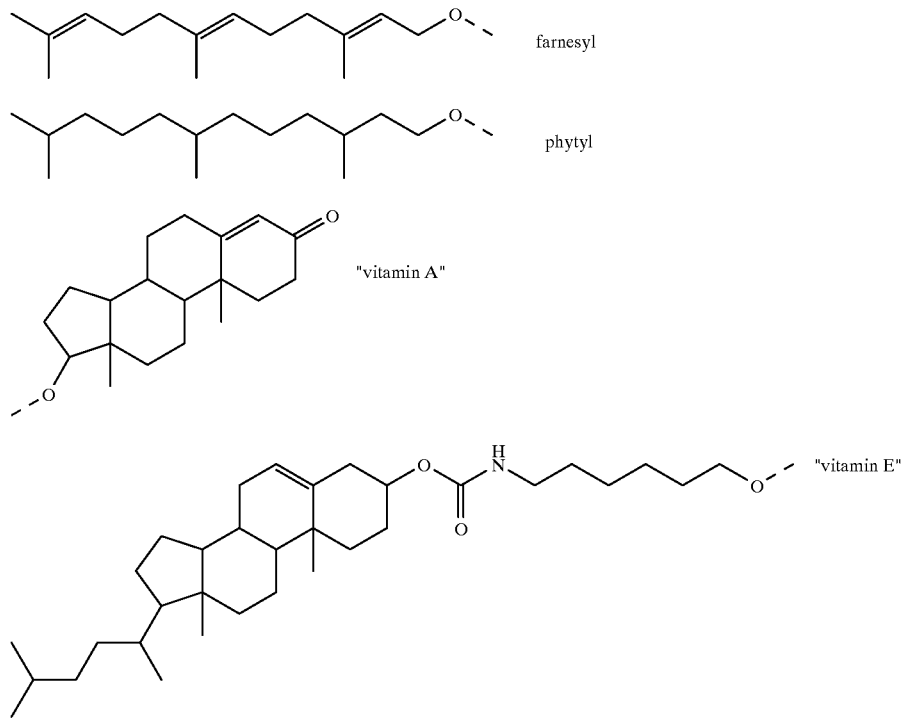

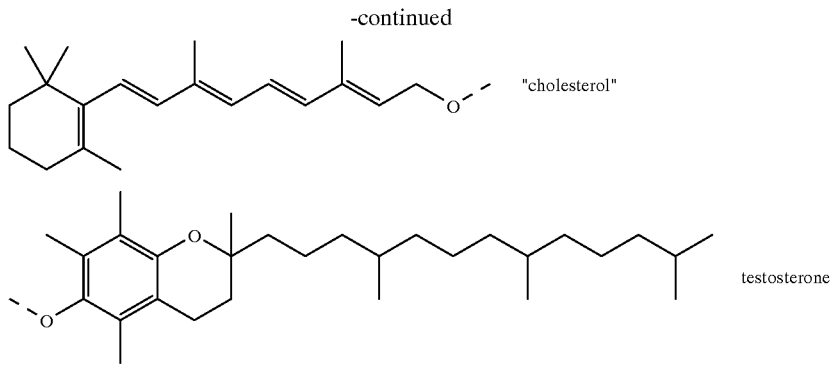

EXAMPLE 6

Testing for Nuclease Stability 10 nmol of the oligonucleotide under investigation are dissolved in 450 μl of 20% strength fetal calf serum in RPMI medium and 50 ml of double-distilled water and incubated at 37° C. 10 μl samples for gel electrophoresis, and 20 μl samples, for HPLC, are then removed immediately and after 1, 2, 4, 7, and 24 hours and in each case mixed with 5 or 10 μl of formamide, respectively, to stop the reaction, and then heated at 95° C. for 5 minutes. For the gel electrophoresis, the samples are loaded onto a 15% polyacrylamide gel (2% bis), which is then run for about 3,000 volt hours. The bands are visualized by silver staining. For the HPLC analysis, the samples are injected onto a Gen-Pak Fax HPLC column (from Waters/Millipore) and chromatographed at 1 ml/min with 5 to 50% Buffer A in B (Buffer A: 10 mM sodium dihydrogen phosphate, 0.1 M NaCl in acetonitrile/water 1:4 (v:v) pH 6.8; Buffer B: as A, but 1.5 M NaCl).

EXAMPLE 7

Antiviral Activity in Tissue Culture

Vero cells ($2 \times 10^5$/ml) are grown in serum-containing Dulbecco's MEM (5% fetal calf serum) in a 96 well microtitre plate for 24 hours at 37° C. and 5% carbon dioxide. The medium is then removed and washed twice with Dulbecco's medium. The compounds are dissolved in double distilled water (600 μM) and diluted with serum-containing medium to give after addition of cells final oligonucleotide concentrations of 40 nM to 80 μM. After 3 hours of incubation of the cells with oligonucleotides, cells are infected with 500 PFU's (plaque forming units) HSV-1 (ATCC VR731; F-strain) or with 350 PFU's HSV-2 (ATCC VR734, G-strain) per well. Incubation is continued for 72 hours in presence of 100 U/ml penicillin and 100 mg/l streptomycin at 37° C. and 5% carbon dioxide. After microscopic evaluation, the tissue culture is stained with neutral red. (Finter's color test) (Finter, N. B. in "Interferons", N. B. Finter et al., North Holland Publishing Co., Amsterdam, 1966).

The antiviral activity or biological activity of an oligonucleotide is defined as the minimal inhibitory concentration (MIC) that is required to protect 30–60% of the cells from the cytopathic effects caused by the virus.

A. Specific examples of tissue culture antiviral activity

Herp 112 (SEQ ID NOS:22–23) and Herp 18 (SEQ ID NOS:24–28) oligonucleotides are directed against HSV-1 mRNA.

This example shows that an oligonucleotide of formula I (e.g. Herp 112b SEQ ID NO:23) (wherein $R_1=R_2=H$, a=oxy, n=19, W=thioxo (as characterized by the "*" below) or oxo, U=hydroxyl or the physiologically tolerated salt, V=Y=oxy, Z=$C_{14}$alkoxy with a tetradecylphosphate residue at the 3'-end) is about 3-times more active than the corresponding 3'-hydroxy compound (e.g. Herp 112a SEQ ID NO:22).

```
Herp 112a   5' G*G*C*GGGGCTCCATGGGGG*T*C-OH        (SEQ ID NO:22)
MIC 10 μM

Herp 112b   5' G*G*C*GGGGCTCCATGGGGG*T*C-p-OC14    (SEQ ID NO:23)
MIC 3 μM
(*means phosphorothioate internucleotide in all examples)
```

The following example of oligos of formula I ($R_1=R_2=H$, a=oxy, n=19, W=thioxo (as characterized by the "*" below) or oxo, U=hydroxyl or the physiologically tolerated salt, V=Y=oxy, Z=an alkoxy varying from $C_{12}$ to $C_{18}$ depending on the specified modification at the 3' end) shows that the biological activity of these modified oligonucleotides depends on the type of 3'-modification:

```
Herp 18     5' G*C*AGGAGGATGCTGAGGA*G*G*C-OH      (SEQ ID NO:24)
MIC ≧ 80 μM
```

-continued

```
Herp 18a    5' G*C*AGGAGGATGCTGAGGA*G*G*C-p-OC₁₂    (SEQ ID NO:25)
MIC 80 µM Herp 18b    5' G*C*AGGAGGATGCTGAGGA*G*G*C-p-OC₁₄    (SEQ ID NO:26)
MIC 27 µM Herp 18c    5' G*C*AGGAGGATGCTGAGGA*G*G*C-p-OC₁₆    (SEQ ID NO:27)
MIC 9 µM Herp 18d    5' G*C*AGGAGGATGCTGAGGA*G*G*C-p-OC₁₈    (SEQ ID NO:28)
MIC 3 µM
```

A control oligonucleotide, which is not complementary to Herpes mRNA (e.g., Kon 2a SEQ ID NO:29), but having the identical chemical derivatization at the 3' end and as a phosphorothioate as Herp 18b (SEQ ID NO:26), is not active:

```
Kon 2a      5' C*C*AGGGTACAGGTGGCCG*G*C*C-p-OC₁₄    (SEQ ID NO:29)
MIC ≧ 80 µM

Herp 18b    5' G*C*AGGAGGATGCTGAGGA*G*G*C-p-OC₁₄    (SEQ ID NO:26)
MIC 27 µM
```

Toxicity occurs at concentrations greater than 80 µM, which means that the effective oligo compounds against HSV-1 are nontoxic.

EXAMPLE 8

Single Cycle Experiments

Similarly, a single cycle assay may be performed as described above in Example 7, except that the time for incubation is reduced from 72 hours to 20 hours, and the antisense compound is added a) 3 hours before infection, b) during infection, or c) 3 hours after infection. Thus, just one single cycle of virus replication should take place within the assay time. The consequence is that virus penetration is not possible within this time frame. This is important because some antisense compounds, like all phosphorothioates or very lipophilic compounds (e.g., cholesterol-modified oligonucleotides), can exert their antiviral effect via virus adsorption blocking or virus penetration blocking. Thus, the Herp 18b (SEQ ID NO:26) is a "true" antisense compound, which is even active 3 hours after viral infection.

EXAMPLE 9

Antiviral activity in vivo

The animals used in the experiments were 5 weeks old NMRI mice weighing 16 to 18 grams. The mice are housed under conventional conditions in groups of 5 animals with food and water ad libitum. Mice are infected intraperitoneally with approximately 10 to 50 LD(50) HSV-1. They are treated once 3 hours after infection and then twice daily, 8 hours apart, for the next four days with the compound administered intraperitoneally at a dose of 1 to 250 mg/kg. Placebo controls are treated with the vehicle (0.9% NaCl) alone. Mortality is monitored for two weeks post infection. In animals without treatment, mortality is 5/5. In animals treated with antisense oligonucleotide, mortality is reduced to 0/5 to 4/5 depending on the sequence, chemical modification and doses used in the study.

EXAMPLE 10

Determination of Cellular Uptake of Oligonucleotides

VERO cells were grown in 96 well culture dishes in DMEM, 5% FCS, 2–10⁴/well, and incubated at 24 h at 37°. Medium was removed and cells were washed two-times with DMEM without FCS.

Add 200 ul medium (without FCS) to "cold" (unphosphorylated) oligo to give 0.98 µM (2.94, 8.9, 26.7 or 80 µM) solutions and $1.10^6$ cpm of "hot" 5'-[$^{32}$P]-labeled oligo (counted by Cherencov or $4.10^6$ cpm) in each well. Alternatively, take $2.10^6$ cpm of [$^{35}$S]-labeled oligo.

Incubate cells with oligo for 1,3,7,18,24 hrs at 37° C. in $CO_2$-incubator.

Take an aliquote of 150 ul of medium from the well and freeze it immediately (to be used for investigation of stability)13 "Supernatant 1".

Wash cells in the well 7-times with 300 ul fresh medium, combine medium in scintillation vial for counting— "Supernatant 2".

Add 100 ul Trypsin, wait for 30 sec, then suction off supernatant and incubate plate at 37° in $CO_2$-incubator for 3 min to detach cells from the dish.

Add 200 ul of DMEM with 10% of FCS to the well; remove cells with pipet and place in 1.5 ml microfuge tube.

Visually inspect well (using microscope) to ensure that most cells have been removed. If necessary, add 200 ul of medium to well to remove any remaining cells. Combine media in appropriate tube.

Centrifuge the cells at 2000 rpm, 6 min, and suction off supernatant—"Supernatant 3".

Transfer 5 ul of "Supernatant 1", 0.5 ml of others supernatants and cells from step 8 and count in vials by Cherencov. Uptake of oligos by the cells may be estimated in pmoles (per 100,000 cells quantity of cells in one well), and expressed as a percentage using the following formula:

Uptake=cpm (pellet)/cpm (total sup.+pellet)×100

| Uptake of Herp 112a | | | | | |
|---|---|---|---|---|---|
| Time of Incubation hrs | Pellets (Cells) | Radioactivity of Supernatants* cpm | total sup. + pel cpm | Uptake by % | the Cells pmoles/ $2 \times 10^5$ Cells |
| 1 | 8805 | 433978 | 442783 | 2 | 4 |
| 3 | 11108 | 329890 | 340998 | 3.2 | 6.52 |
| 8 | 18669 | 449356 | 468025 | 3.99 | 7.98 |
| 14 | 19909 | 467112 | 487021 | 4.08 | 8.16 |
| 24 | 29862 | 683592 | 713454 | 4.18 | 8.36 |

*Supernatants cpm = total cpms for supernatants 1 + 2 + 3

| Uptake of Herp 112b | | | | | |
|---|---|---|---|---|---|
| Time of Incubation hrs | Pellets (Cells) | Radioactivity of Supernatants* | total sup. + pel cpm | Uptake by % | The Cells pmoles/ $2 \times 10^5$ cells |
| 1 | 6965 | 204709 | 211674 | 3.2 | 6.4 |
| 3 | 9423 | 246948 | 256371 | 3.7 | 7.4 |
| 8 | 6672 | 182850 | 189522 | 3.5 | 7.0 |
| 14 | 11085 | 252280 | 263365 | 4.2 | 8.4 |
| 24 | 12209 | 254390 | 263599 | 4.63 | 9.26 |

*Supernatants cpm = total cpm for supernatants 1 + 2 + 3

Uptake of Herp 18 and 18c and control oligonucleotides Kon 2 and 2b
Time of incubation: 24 hrs (concentration oligonucleotide 5 μmol

| Oligo-Nr. | Supernatants 0.5 ml · cpm | Volume | total super | Pellet: (Cells) · cpm | total cpm | Uptake by % | the Cells mmol/$2 \times 10^5$ Cells |
|---|---|---|---|---|---|---|---|
| Herp 18c | 281000 | 2 ml | 1124000 | 7655 | 1131655 | 0.67 | 6.7 |
| Kon 2b | 754420 | 2 ml | 3017680 | 18350 | 3036030 | 0.60 | 6.0 |
| Herp 18 | 948980 | 2 ml | 3795920 | 5533 | 3801453 | 0.1455 | 1.4 |
| Kon | 1980560 | 2 ml | 7922270 | 7592 | 7929832 | 0.0957 | 0.96 |

Therefore, the uptake of Herp 112b (SEQ ID NO:23) was found to be 20% higher as compared to Herp 112a (SEQ ID NO:22) in Vero cells at an external concentration of 1 μM oligonucleotide and 37° C.

```
Herp 112a    5' G*G*C*GGGGCTCCATGGGGG*T*C-OH        (SEQ ID NO:22)

MIC 10 μM

Herp 112b    5' G*G*C*GGGGCTCCATGGGGG*T*C-p-OC₁₄    (SEQ ID NO:23)

MIC 3 μM
```

The cellular uptake of a hexadecyl-phosphate antisense oligonucleotide (e.g., Herp 18c SEQ ID NO:27) was about 5-times as high as the corresponding hydroxy-compound (e.g., Herp 18 SEQ ID NO:24). The lipophilic compound is about 10-times more active than the nonmodified compound (e.g., Herp 18 SEQ ID NO:24)

```
Herp 18      5' G*C*AGGAGGATGCTGAGGA*G*G*C-OH          (SEQ ID NO:24)

MIC ≧ 80µM

Herp 18c     5' G*C*AGGAGGATGCTGAGGA*G*G*C-p-OC₁₆      (SEQ ID NO:27)

MIC 9 µM
```

A control oligonucleotide will also show enhanced cellular uptake if a hexadecyl residue is conjugated to the 3'-end (e.g., Kon 2b SEQ ID NO:31). These compounds are inactive against HSV-1, (see result of single cycle experiment above in Example 8).

```
Kon 2  5' C*C*AGGGTACAGGTGGCCG*G*C*C-OH         (SEQ ID NO:30)
Kon 2b 5' C*C*AGGGTACAGGTGGCCG*G*C*C-p-OC₁₆     (SEQ ID NO:31)
```

It will be apparent to those skilled in the art that various modifications and variations can be made to the present invention and in construction of this invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

We claim:

1. An oligonucleotide analog of the formula I

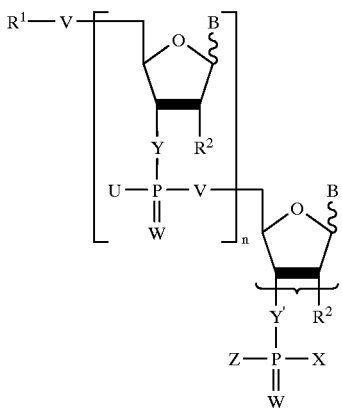 (I)

wherein:

$R^1$ is hydrogen, $C_1$–$C_{18}$-alkyl, $C_2$–$C_{18}$-alkenyl, $C_2$–$C_{18}$-alkynyl, $C_2$–$C_{18}$-alkylcarbonyl, $C_3$–$C_{19}$-alkenylcarbonyl, $C_3$–$C_{19}$-alkynylcarbonyl, $C_6$–$C_{20}$-aryl, ($C_6$–$C_{14}$)-aryl-($C_1$–$C_8$-alkyl), or a radical of the formula II

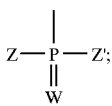 (II)

$R^2$ is hydrogen, hydroxyl, $C_1$–$C_{18}$-alkoxy, halogen, azido or $NH_2$;

B is a conventional base in nucleotide chemistry;

a is oxy or methylene;

n is a number from 1 to 100;

W is oxo, thioxo or selenoxo;

V is oxy, thio, or imino;

Y is oxy, thio, imino or methylene;

Y' is oxy, thio, imino or $(CH_2)_m$ or $V(CH_2)_m$;

m is a number from 1 to 18;

X is hydroxyl or mercapto;

U is hydroxyl, mercapto, SeH, $C_1$–$C_{18}$-alkoxy, $C_1$–$C_{18}$-alkyl, $C_6$–$C_{20}$-aryl, ($C_6$–$C_{14}$)-aryl-($C_1$–$C_8$)-alkyl, $NHR^3$, $NR^3R^4$ or a radical of the formula III

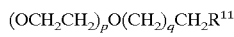 (III)

$R^3$ is $C_1$–$C_{18}$-alkyl, $C_6$–$C_{20}$-aryl, ($C_6$–$C_{14}$)-aryl-($C_1$–$C_8$)-alkyl or $2\text{-}(CH_2)_c\text{-}[NH(CH_2)_c]_d\text{-}NR^{12}R^{12}$;

c is a number from 2 to 6;

d is a number from 0 to 6;

$R^{12}$ is independently hydrogen, $C_1$–$C_6$-alkyl or $C_1$ $C_4$-alkoxy-$C_1$–$C_6$-alkyl;

$R^4$ is $C_1$–$C_{18}$-alkyl, $C_6$–$C_{20}$-aryl or ($C_6$–$C_{10}$)-aryl-($C_1$–$C_8$)-alkyl, or in the case of $NR^3R^4$ is, together with $R^3$ and the nitrogen atom carrying them, a 5-6-membered heterocyclic ring, which can additionally contain a further hetero atom selected from the group comprising O, S and N;

p is a number from 1 to 100;

q is a number from 0 to 22;

$R^{11}$ is hydrogen or a functional group;

Z=Z' are hydroxyl; mercapto; SeH; $C_1$–$C_{22}$-alkoxy; —O—$(CH_2)_b$-$NR^{12}R^{13}$, where b is a number from 1 to 6, and $R^{13}$ is $C_1$–$C_6$-alkyl, or $R^{12}$ and $R^{13}$ together with the nitrogen atom carrying them form a 3-6-membered ring;

$C_1$–$C_{18}$-alkyl; $C_6$–$C_{20}$-aryl; ($C_6$–$C_{14}$)-aryl-($C_1$–$C_8$)-alkyl; ($C_6$–$C_{14}$)-aryl-($C_1$–$C_8$)-alkoxy, where aryl is optionally substituted by 1, 2 or 3 identical or different radicals selected from the group comprising carboxyl, amino, nitro, $C_1$–$C_4$-alkylamino, $C_1$–$C_6$-alkoxy, hydroxyl, halogen and cyano;

$C_1$–$C_{18}$-alkyl-mercapto; $NHR^3$; $NR^3R^4$; a radical of the formula III; or a group which favors intracellular uptake with the proviso that heteroaryl moieties containing 1 or 2 nitrogen atoms are excluded, or serves as the label for a DNA probe, or, during hybridization of the oligonucleotide analog to the target nucleic acid, attacks the latter with binding, crosslinking or cleavage, with the proviso that Z includes no functional moieties arising through cleavage of Z from a support; the curved bracket indicates that $R^2$ and the neighboring phosphoryl residue can be located in the 2'- and 3'-position or else the opposite way round in the 3'- and 2'-position, where each nucleotide can be present in its D- or L-configuration and the base B can be located in the α- or β-position, with the proviso that, if Z is hydroxyl, mercapto, methyl or ethoxy, at least one of the groups X, Y, Y', V and W is not hydroxyl, oxy or oxo, or $R^1$ is not hydrogen or methylphosphonate monoester;

or a physiologically tolerable salt thereof.

2. An oligonucleotide analog as claimed in claim 1, wherein the base B is located in the β-position, the nucleotides are present in the D-configuration, $R^2$ is located in the 2'-position, and a is oxy.

3. The oligonucleotide analog as claimed in claim 1, wherein:

$R^1$ is hydrogen, $C_1$–$C_6$-alkyl, or a radical of the formula II as defined in claim 1;

$R^2$ is hydrogen or hydroxyl;

n is a number from 10 to 40;

m is a number from 1 to 6;

U is hydroxyl, mercapto, $C_1$–$C_6$-alkyl, or methoxyethyl, and B, W, V, X, Y, Y' and Z are defined as in claim 1.

4. The oligonucleotide analog as claimed in claim 1, wherein V, Y and Y' are oxy.

5. The oligonucleotide analog as claimed in claim 1, wherein W is oxo.

6. The oligonucleotide as claimed in claim 1, wherein U is hydroxyl.

7. The oligonucleotide analog as claimed in claim 1, wherein $R^1$ is hydrogen.

8. The oligonucleotide analog as claimed in claim 3, wherein $R^1$ is $C_1$–$C_6$-alkyl, $R^2$ is hydrogen, n is 12 to 30, m is 1, U is hydroxyl or $C_1$–$C_6$-alkyl, and $R^3$ is $C_1$–$C_4$-alkyl.

9. A pharmaceutical composition comprising at least one oligonucleotide analog of the formula I as claimed in claim 1, or a physiologically tolerable salt thereof, and either or both of a physiologically tolerated adjuvant or an excipient.

10. A process for preparing an oligonucleotide analog of the formula I as claimed in claim 1, wherein a) a nucleotide unit with a 3'(2')-terminal phosphorus(V) grouping and a free 5'-hydroxyl or mercapto group is reacted with another nucleotide unit with a phosphorus (III) or phosphorus (V) grouping in the 3' position and a temporarily protected 5'-hydroxyl or mercapto group, or their activated derivatives, b) the oligonucleotide analog is constructed with fragments in a similar manner, and protective groups, which have been temporarily introduced in the oligonucleotides obtained according to (a) or (b) in order to protect other functions, are removed and the oligonucleotide analog of the formula I thus obtained is, where appropriate, converted into its physiologically tolerated salt.

11. A process for inhibiting gene expression comprising the step of contacting a gene, an mRNA transcript of a gene or a nucleic acid-binding protein capable of binding to the gene, with an oligonucleotide analog as claimed in claim 1, in an amount effective to inhibit expression of the gene.

12. A process for inhibiting gene expression by contacting a gene, an mRNA transcript of a gene or a nucleic acid-binding protein capable of binding to the gene, with an oligonucleotide analog in an amount effective to inhibit expression of the gene, wherein the improvement comprises using the oligonucleotide analog as claimed in claim 1.

* * * * *

UNITED STATES PATENT AND TRADEMARK OFFICE
CERTIFICATE OF CORRECTION

PATENT NO. : 6,033,909  Page 1 of 1
DATED : March 7, 2000
INVENTOR(S) : Uhlmann et al.

It is certified that error appears in the above-identified patent and that said Letters Patent is hereby corrected as shown below:

Column 59,
Line 56, "$[NH(CH_2)_{c]d}$" should read -- $[NH(CH_2)\ _c]_d$ --.
Line 60, "$C_1C_4$-" should read -- $C_1$-$C_4$- --.

Column 60,
Line 37, "$R^2is$" should read -- $R^2$ is --.

Column 61,
Line 1, "phosphous(V)" should read -- phosphorus (V): --.

Signed and Sealed this

Twelfth Day of November, 2002

Attest:

JAMES E. ROGAN
Attesting Officer  Director of the United States Patent and Trademark Office